(12) United States Patent
Kato et al.

(10) Patent No.: US 7,700,618 B2
(45) Date of Patent: Apr. 20, 2010

(54) SULFONYL BENZIMIDAZOLE DERIVATIVES

(75) Inventors: Tomoki Kato, Chita-gun (JP); Kana Kon-I, Chita-gun (JP); Yohei Yuki, Chita-gun (JP); Kazuo Ando, Chita-gun (JP)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 12/280,586

(22) PCT Filed: Feb. 23, 2007

(86) PCT No.: PCT/IB2007/000474

§ 371 (c)(1),
(2), (4) Date: Jan. 29, 2009

(87) PCT Pub. No.: WO2007/102059

PCT Pub. Date: Sep. 13, 2007

(65) Prior Publication Data

US 2009/0137584 A1  May 28, 2009

Related U.S. Application Data

(60) Provisional application No. 60/795,354, filed on Apr. 26, 2006, provisional application No. 60/779,776, filed on Mar. 6, 2006.

(51) Int. Cl.
*A61K 31/437* (2006.01)
*A61K 31/4184* (2006.01)
*C07D 471/04* (2006.01)
*C07D 235/08* (2006.01)

(52) U.S. Cl. .............. 514/303; 546/118; 514/394; 548/304.4

(58) Field of Classification Search .......... None
See application file for complete search history.

(56) References Cited

U.S. PATENT DOCUMENTS

2006/0094750 A1* 5/2006 Kon-I et al. .............. 514/303

FOREIGN PATENT DOCUMENTS

WO  WO 02/085866  10/2002
WO  WO 2005/030762  4/2005
WO  WO 2006/048754  5/2006

* cited by examiner

*Primary Examiner*—Rei-Tsang Shiao
*Assistant Examiner*—Alicia L Fierro
(74) *Attorney, Agent, or Firm*—Gregg C. Benson; J. Michael Dixon; Garth Butterfield

(57) ABSTRACT

This invention relates to compounds of the formula (I): or a pharmaceutically acceptable salt thereof, wherein A, $R^1$, $R^2$, $R^3$, $R^4$, $R^5$, m and n are each as described herein, and compositions containing such compounds, and the use of such compounds in the treatment of a condition mediated by CB2 receptor activity such as, but not limited to, inflammatory pain, nociceptive pain, neuropathic pain, fibromyalgia, chronic low back pain, visceral pain, acute cerebral ischemia, pain, chronic pain, acute pain, post herpetic neuralgia, neuropathies, neuralgia, diabetic neuropathy, HIV-related neuropathy, nerve injury, rheumatoid arthritic pain, osteoarthritic pain, back pain, cancer pain, dental pain, fibromyalgia, neuritis, sciatica, inflammation, neurodegenerative disease, cough, broncho constriction, irritable bowel syndrome (IBS), inflammatory bowel disease (IBD), colitis, cerebrovascular ischemia, emesis such as cancer chemotherapy-induced emesis, rheumatoid arthritis, asthma, Crohn's disease, ulcerative colitis, asthma, dermatitis, seasonal allergic rhinitis, GERD, constipation, diarrhea, functional gastrointestinal disorders, irritable bowel syndrome, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, COPD, cryptogenic fibrosing alveolitis and bronchitis.

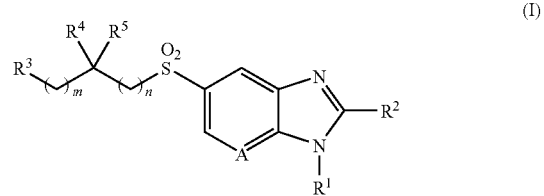

(I)

7 Claims, No Drawings

SULFONYL BENZIMIDAZOLE DERIVATIVES

CROSS REFERENCE

This application is the nationalization under 37 U.S.C. 371 of International Application Number PCT/IB2007/000474 filed Feb. 23, 2007 which claims the benefits of U.S. Provisional Application 60/779,776 filed Mar. 6, 2006 and U.S. Provisional Application 60/795,354, filed Apr. 26, 2006.

BACKGROUND OF THE INVENTION

This invention relates to sulfonyl benzimidazole derivatives. These compounds have selective cannabinoid (CB)2 receptor agonistic activity. The present invention also relates to a pharmaceutical composition, method of treatment and use, comprising the above derivatives for the treatment of disease conditions mediated by CB2 receptor activity; in particular CB2 receptor agonistic activity.

In general, CB2 receptor agonists are found to be useful for the treatment of a variety of diseases, including inflammatory pain, nociceptive pain, neuropathic pain, fibromyalgia, chronic low back pain, visceral pain, rheumatoid arthritis, Crohn's disease, ulcerative colitis, asthma, dermatitis, seasonal allergic rhinitis, gastroesophageal reflux disease (GERD), constipation, diarrhea, functional gastrointestinal disorder, irritable bowel syndrome, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, chronic obstructive pulmonary disease (COPD), cryptogenic fibrosing alveolitis and bronchitis (see *J Pharmacol Exp Ther.* 2004 February; 308(2):446-53; *Proc Natl Acad Sci USA.* 2003 Sep. 2; 100(18):10529-33; *Br J Pharmacol.* 2004 August; 142(8):1247-54).

WO02/85866 discloses sulfonylamide compounds as CB2 agonists. Especially, compounds represented by the following formula is disclosed as Example 68:

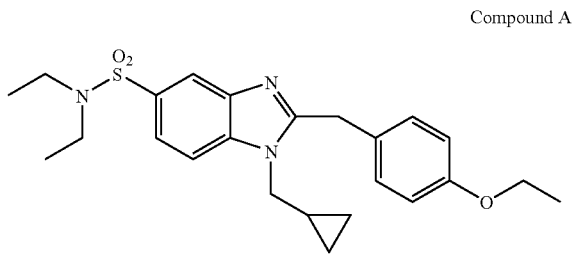

Compound A

There is a need to provide new CB2 agonists that can be a good drug. In particular, preferred compounds should bind potently to the CB2 receptor whilst showing little affinity for other receptors and show functional activity as agonists. They should be well absorbed from the gastrointestinal tract, be metabolically stable and possess favorable pharmacokinetic properties. When targeted against receptors in the central nervous system they should cross the blood brain barrier freely. They should be non-toxic. Furthermore, the ideal drug candidate will exist in a physical form that is stable, non-hygroscopic and easily formulated.

SUMMARY OF THE INVENTION

In this invention, it has now been found out that a new class of benzimidazole compounds having an alkylsulfonyl group at the 5-position and an aliphatic group at the 2-position show CB2 agonistic activity and favorable properties as drug candidates, and thus are useful for the treatment of disease conditions mediated by CB2 activity such as inflammatory pain, nociceptive pain, neuropathic pain, fibromyalgia, chronic low back pain, visceral pain, acute cerebral ischemia, pain, chronic pain, acute pain, post herpetic neuralgia, neuropathies, neuralgia, diabetic neuropathy, HIV-related neuropathy, nerve injury, rheumatoid arthritic pain, osteoarthritic pain, back pain, cancer pain, dental pain, fibromyalgia, neuritis, sciatica, inflammation, neurodegenerative disease, cough, broncho constriction, irritable bowel syndrome (IBS), inflammatory bowel disease (IBD), colitis, cerebrovascular ischemia, emesis such as cancer chemotherapy-induced emesis, rheumatoid arthritis, Crohn's disease, ulcerative colitis, asthma, dermatitis, seasonal allergic rhinitis, GERD, constipation, diarrhea, functional gastrointestinal disorders, irritable bowel syndrome, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, COPD, cryptogenic fibrosing alveolitis and bronchitis (hereinafter, referred as 'CB2 Diseases').

The present invention provides a compound of the following formula (I):

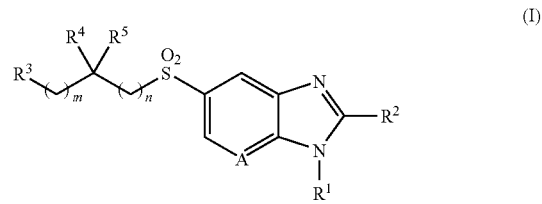

(I)

wherein
A is carbon or nitrogen;
$R^1$ is $C_1$-$C_4$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl) amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl;
$R^2$ is cycloalkyl, alkyl-substituted cycloalkyl, $C_3$-$C_{10}$ alkyl, alkoxy-substituted $C_3$-$C_{10}$ alkyl or $C_1$-$C_2$ alkyl, said $C_1$-$C_2$ alkyl being substituted with 1 to 2 substituents independently selected from the group consisting of cycloalkyl and alkyl-substituted cycloalkyl;
$R^3$ is —$NR^aCO$—$NR^bR^c$, —$NR^aCO$—($C_1$-$C_4$ alkyl), —CO—$NR^bR^c$, —$NR^aSO_2$—$NR^bR^c$ or —$NR^aSO_2$—($C_1$-$C_4$ alkyl),
wherein
$R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; or alternatively $R^b$ and $R^c$ together with nitrogen atom to which they are attached form a 5 to 6 membered ring;

$R^4$ and $R^5$ are independently selected from the group consisting of hydrogen, halogen, $C_1$-$C_4$ alkyl and $C_1$-$C_4$ alkoxy; or alternatively $R^4$ and $R^5$ together with the carbon atom to which they are attached form a 3 to 6 membered ring; and m and n are independently selected from 0, 1 or 2;

or a pharmaceutically acceptable salt thereof.

Also, the present invention provides the use of a compound of formula (I) or a pharmaceutically acceptable salt thereof, each as described herein, for the manufacture of a medicament for the treatment of a condition mediated by CB2 receptor activity; in particular, CB2 agonistic activity.

Preferably, the present invention also provides the use of a compound of formula (I) or a pharmaceutically acceptable salt thereof, each as described herein, for the manufacture of a medicament for the treatment of diseases selected from CB2 Diseases.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and another pharmacologically active agent.

Further, the present invention provides a method of treatment of a condition mediated by CB2 receptor activity, in a mammalian subject, which comprises administering to a mammal in need of such treatment a therapeutically effective amount of a compound of formula (I) or a pharmaceutically acceptable salt thereof, each as described herein.

Examples of conditions mediated by CB2 receptor activity include, but are not limited to, CB2 Diseases.

The compounds of the present invention may show less toxicity, good absorption, distribution, good solubility, less protein binding affinity other than CB2 receptor, less drug-drug interaction, and good metabolic stability.

DETAILED DESCRIPTION OF THE INVENTION

In the compounds of the present invention:

Where $R^1$ is substituted $C_1$-$C_4$ alkyl, or $R^4$, $R^5$, $R^a$, $R^b$ or $R^c$ is $C_1$-$C_4$ alkyl, or one or more substituents of $R^1$ is $C_1$-$C_4$ alkyl, this $C_1$-$C_4$ alkyl group may be a straight or branched chain group, and examples include, but are not limited to, methyl, ethyl, propyl, isopropyl, butyl, isobutyl, sec-butyl and tert-butyl. Of these, methyl and ethyl are preferred for $R^1$ and $R^a$; isopropyl is preferred for the substituent of $R^1$.

Where $R^2$ is $C_3$-$C_{10}$ alkyl, this may be a straight or branched chain group, and examples include, but are not limited to, propyl, isopropyl, butyl, isobutyl, sec-butyl, tert-butyl, pentyl, 2,2-dimethylpropyl, hexyl, 2,2-dimethylbutyl, 3,3-dimethylbutyl, 1,2,2-trimethylpropyl, heptyl, 4,4-dimethylpentyl, 2,3,3-trimethylbutyl, octyl, 5,5-dimethylhexyl, 2,4,4-trimethylpentyl, nonyl, 6,6-dimethylheptyl, 2,5,5-trimethylhexyl, decyl, 7,7-dimethyloctyl and 2,6,6-trimethylheptyl. Of these, branched $C_4$-$C_8$ alkyl is preferred; tert-butyl, 2,2-dimethylpropyl, 2,2-dimethylbutyl and 2,4,4-trimethylpentyl are more preferred; tert-butyl and 2,2-dimethylpropyl are most preferred.

Where $R^4$, $R^5$ or one or more substituents of $R^1$ is $C_1$-$C_4$ alkoxy, the $C_1$-$C_4$ alkyl moiety of said alkoxy may be straight or branched. Examples of such $C_1$-$C_4$ alkoxy include, but are not limited to, methoxy, ethoxy, propyloxy, isopropyloxy, butyloxy, isobutyloxy, sec-butyloxy and tert-butyloxy. Of these, methoxy is preferred.

Where $R^a$, $R^b$ or $R^c$, or one or more substituents of $R^1$ is $C_1$-$C_4$ alkylamino, the $C_1$-$C_4$ alkyl moiety of said alkylamino may be straight or branched. Examples of such $C_1$-$C_4$ alkylamino groups include, but are not limited to, methylamino, ethylamino, propylamino, isopropylamino, butylamino, isobutylamino, sec-butylamino and tert-butylamino. Of these, $C_1$-$C_2$ alkylamino is preferred; methylamino is more preferred.

Where $R^a$, $R^b$ or $R^c$, or one or more substituents of $R^1$ is di($C_1$-$C_4$ alkyl)amino, the $C_1$-$C_4$ alkyl moieties of said di($C_1$-$C_4$ alkyl)amino may be straight or branched. Examples of such di($C_1$-$C_4$ alkyl)amino include, but are not limited to, dimethylamino, N-methyl-N-ethylamino, diethylamino, dipropylamino, diisopropylamino, dibutylamino, diisobutylamino, and N,N-di(1-methylpropyl)amino. Of these, di($C_1$-$C_3$)alkylamino is preferred; dimethylamino and diethylamino are more preferred.

Where $R^a$, $R^b$ or $R^c$ is $C_1$-$C_4$ alkylaminocarbonyl, the $C_1$-$C_4$ alkyl moiety of said alkylaminocarbonyl may be straight or branched. Examples of such $C_1$-$C_4$ alkylaminocarbonyl include, but are not limited to, methylaminocarbonyl, ethylaminocarbonyl, propylaminocarbonyl, isopropylaminocarbonyl, butylaminocarbonyl, isobutylaminocarbonyl, sec-butylaminocarbonyl and tert-butylaminocarbonyl. Of these, $C_1$-$C_2$ alkylaminocarbonyl is preferred; methylaminocarbonyl is more preferred.

Where $R^a$, $R^b$ or $R^c$ is di($C_1$-$C_4$ alkyl)aminocarbonyl, the $C_1$-$C_4$ alkyl moieties of said di($C_1$-$C_4$ alkyl)aminocarbonyl may be straight or branched. Examples of such di($C_1$-$C_4$ alkyl)aminocarbonyl include, but are not limited to, dimethylaminocarbonyl, N-methyl-N-ethylaminocarbonyl, diethylaminocarbonyl, dipropylaminocarbonyl, diisopropylaminocarbonyl, dibutylaminocarbonyl, diisobutylaminocarbonyl, and N,N-di(1-methylpropyl)aminocarbonyl. Of these, di($C_1$-$C_3$)alkylaminocarbonyl is preferred; dimethylaminocarbonyl and diethylaminocarbonyl are more preferred.

Where $R^2$ is alkoxy-substituted $C_3$-$C_{10}$ alkyl, this alkoxy-substituted $C_3$-$C_{10}$ alkyl represents $C_1$-$C_4$ alkoxy-substituted $C_3$-$C_{10}$ alkyl, and $C_1$-$C_4$ alkoxy and $C_3$-$C_{10}$ alkyl groups are as described above. Examples of an alkoxy-substituted $C_3$-$C_{10}$ alkyl group include, but are not limited to, 3-methoxypropyl, 2-methoxy-1-methylethyl, 4-methoxybutyl, 3-methoxy-2-methylpropyl, 3-ethoxy-2-methylpropyl, 5-methoxypentyl, 3-methoxy-2,2-dimethylpropyl, 3-ethoxy-2,2-dimethylpropyl, 6-methoxyhexyl, 4-methoxy-3,3-dimethylbutyl, 3-methoxy-1,2,2-trimethylpropyl, 7-methoxyheptyl, 5-methoxy-4,4-dimethylpentyl, 4-methoxy-2,3,3-trimethylbutyl, 6-methoxy-5,5-dimethylhexyl, 5-methoxy-2,4,4-trimethylpentyl, 5-ethoxy-2,4,4-trimethylpentyl, 7-methoxy-6,6-dimethylheptyl, 6-methoxy-2,5,5-trimethylhexyl, 8-methoxy-7,7-dimethyloctyl and 7-methoxy-2,6,6-trimethylheptyl. Of these, the alkoxy-substituted branched $C_4$-$C_8$ alkyl is preferred; 3-methoxy-2-methylpropyl, 3-methoxy-2,2-dimethylpropyl and 5-methoxy-2,4,4-trimethylpentyl are more preferred; 3-methoxy-2,2-dimethylpropyl is most preferred.

Where $R^2$ or one or more substituents of $R^1$ or one or more substituents of $R^2$ is cycloalkyl, this represents $C_3$-$C_7$ cycloalkyl. Examples include, but are not limited to, cyclopropyl, cyclobutyl, cyclopentyl, cyclohexyl and cycloheptyl. Of these, $C_3$-$C_5$ cycloalkyl is preferred; cyclopropyl is more preferred.

Where $R^2$, one or more substituents of $R^1$ or one or more substituents of $R^2$ is alkyl-substituted cycloalkyl, this alkyl-substituted cycloalkyl represents $C_1$-$C_4$ alkyl-substituted $C_3$-$C_7$ cycloalkyl group, and this $C_1$-$C_4$ alkyl group is as described above. Examples of such alkyl-substituted cycloalkyl groups include, but are not limited to, 1-methylcyclopropyl, 2-methylcyclopropyl, 2,2-dimethylcyclopropyl, 2,2,3,3-tetramethylcyclopropyl, 1-methylcyclobutyl, 1 methylcyclopentyl, 1-methylcyclohexyl and 1-methylcycloheptyl. Of these, alkyl-substituted $C_3$-$C_5$ cycloalkyl is preferred; 2,2,3,3-tetramethylcyclopropyl and 2,2-dimethylcyclopropyl are more preferred for $R^2$; 1-methylcyclopropyl and 1-methylcyclopentyl are more preferred for $R^1$ and the substituent of $R^2$.

Where one or more substituents of $R^1$ is hydroxy-substituted cycloalkyl, this hydroxy-substituted cycloalkyl represents hydroxy-substituted $C_3$-$C_7$ cycloalkyl. Examples of hydroxy-substituted cycloalkyl include, but are not limited to, 1-hydroxycyclopropyl, 2-hydroxycyclopropyl, 1-hydroxycyclobutyl, 2-hydroxycyclobutyl, 3-hydroxycyclobutyl 1-hydroxycyclopentyl, 2-hydroxycyclopentyl, 3-hydroxycyclopentyl, 1-hydroxycyclohexyl, 2-hydroxycyclohexyl, 3-hydroxycyclohexyl, 4-hydroxycyclohexyl, 1-hydroxycycloheptyl, 2-hydroxycycloheptyl, 3-hydroxycycloheptyl and 4-hydroxycycloheptyl. Of these, hydroxy-substituted $C_5$-$C_6$ cycloalkyl is preferred; 1-hydroxycyclopentyl and 1-hydroxycyclohexyl are more preferred.

Where one or more substituents of $R^1$ is amino-substituted cycloalkyl, this amino-substituted cycloalkyl represents amino-substituted $C_3$-$C_7$ cycloalkyl. Examples of amino-substituted cycloalkyl include, but are not limited to, 1-aminocyclopropyl, 2-aminocyclopropyl, 1-aminocyclobutyl, 2-aminocyclobutyl, 3-aminocyclobutyl 1-aminocyclopentyl, 2-aminocyclopentyl, 3-aminocyclopentyl 1-aminocyclohexyl, 2-aminocyclohexyl, 3-aminocyclohexyl, 4-aminocyclohexyl, 1-aminocycloheptyl, 2-aminocycloheptyl, 3-aminocycloheptyl and 4-aminocycloheptyl. Of these, amino-substituted $C_5$-$C_6$ cycloalkyl is preferred; 1-aminocyclopentyl and 1-aminocyclohexyl are more preferred.

Where one or more substituents of $R^1$ is heterocyclyl, this represents a 3 to 6-membered ring containing at least one hetero atom selected from N, O and S. Examples include, but are not limited to, oxyranyl, 1-pyrrolidinyl, 2-pyrrolidinyl, 1-imidazolidinyl, 2-tetrahydrofuranyl, 1-piperidinyl, 2-piperidinyl, 1-piperazinyl, 2-tetrahydropyranyl, 4-tetrahydropyranyl, 4-morpholinyl, 4-thiomorpholinyl, 2-thienyl, 2-furyl, 2-thiazolyl, 2-oxazolyl, 2-pyridyl, 3-pyridyl, 4-pyridyl, 2-pyrazyl and 2-pyrimidinyl. Of these, heterocyclyl groups containing at least one nitrogen atom are preferred; 1-pyrrolidinyl, 1-piperidinyl and 4-morpholinyl are more preferred.

Where one or more substituents of $R^1$ is alkyl-substituted heterocyclyl, this alkyl-substituted heterocyclyl group represents a $C_1$-$C_4$ alkyl-substituted heterocyclyl group and the $C_1$-$C_4$ alkyl and heterocyclyl moieties are as described above. Examples of an alkyl-substituted heterocyclyl include, but are not limited to, 2-methyloxyranyl, 3-methyl-1-pyrrolidinyl, 1-methyl-2-pyrrolidinyl, 1-ethyl-2-pyrrolidinyl, 4-methyl-1-imidazolidinyl, 3-methyl-2-tetrahydrofuranyl, 2-methyl-1-piperidinyl, 1-methyl-2-piperidinyl, 1-ethyl-2-piperidinyl, 4-methyl-1-piperazinyl, 2-methyl-1-piperazinyl, 4-methyl-4-tetrahydropyranyl, 3-methyl-4-morpholinyl, 3-methyl-4-thiomorpholinyl, 3-methyl-2-thienyl, 3-methyl-2-furyl, 4-methyl-2-thiazolyl, 4-methyl-2-oxazolyl, 3-methyl-2-pyridyl, 2-methyl-3-pyridyl, 2-methyl-4-pyridyl, 3-methyl-2-pyrazyl and 4-methyl-2-pyrimidinyl. Of these, alkyl-substituted heterocyclyl groups containing at least one nitrogen atom are preferred; 1-methyl-2-pyrrolidinyl and 1-methyl-2-piperidinyl are more preferred.

Where one or more substituents of $R^1$ is hydroxy-substituted heterocyclyl, this heterocyclyl is as described above, and examples of hydroxy-substituted heterocyclyl include, but are not limited to, 3-hydroxy-1-pyrrolidinyl, 4-hydroxy-2-pyrrolidinyl, 3-hydroxy-2-tetrahydrofuranyl, 4-hydroxy-2-tetrahydrofuranyl, 3-hydroxy-3-tetrahydrofuranyl, 4-hydroxy-3-tetrahydrofuranyl, 3-hydroxy-2-tetrahydropyranyl, 4-hydroxy-2-tetrahydropyranyl, 5-hydroxy-2-tetrahydropyranyl, 3-hydroxy-3-tetrahydropyranyl, 4-hydroxy-3-tetrahydropyranyl, 5-hydroxy-3-tetrahydropyranyl, 3-hydroxy-4-tetrahydropyranyl, 4-hydroxy-4-tetrahydropyranyl, 3-hydroxy-2-pyrrolidinyl, 3-hydroxy-3-pyrrolidinyl, 4-hydroxy-3-pyrrolidinyl, 3-hydroxy-1-piperidinyl, 3-hydroxy-2-piperidinyl, 3-hydroxy-3-piperidinyl, 3-hydroxy-4-piperidinyl, 5-hydroxy-3-piperidinyl, 5-hydroxy-2-piperidinyl, 4-hydroxy-1-piperidinyl, 4-hydroxy-2-piperidinyl, 4-hydroxy-3-piperidinyl, 4-hydroxy-4-piperidinyl, 3-hydroxy-2-thienyl, 4-hydroxy-2-thienyl, 5-hydroxy-2-thienyl, 3-hydroxy-2-furyl, 4-hydroxy-2-furyl, 5-hydroxy-2-furyl, 4-hydroxy-2-thiazolyl, 5-hydroxy-2-thiazolyl, 4-hydroxy-2-oxazolyl, 5-hydroxy-2-oxazolyl, 3-hydroxy-2-pyridyl, 4-hydroxy-2-pyridyl, 5-hydroxy-2-pyridyl, 6-hydroxy-2-pyridyl, 2-hydroxy-3-pyridyl, 4-hydroxy-3-pyridyl, 5-hydroxy-3-pyridyl, 6-hydroxy-3-pyridyl, 2-hydroxy-4-pyridyl, 3-hydroxy-4-pyridyl, 3-hydroxy-2-pyrazyl 5-hydroxy-2-pyrazyl, 6-hydroxy-2-pyrazyl, 4-hydroxy-2-pyrimidinyl and 5-hydroxy-2-pyrimidinyl. Of these, hydroxy-substituted heterocyclyl groups containing at least one oxygen atom in the heterocyclyl group are preferred; 4-hydroxy-4-tetrahydropyranyl is more preferred.

Where $R^4$ or $R^5$ is halogen, this halogen may be fluorine, chlorine, bromine, or iodine. Of these, fluorine and chlorine are preferred.

Where $R^4$ and $R^5$ together with the carbon atom to which they are attached form a 3 to 6 membered ring, this 3 to 6 membered ring represents 3 to 6 membered carbocyclic ring or 3 to 6 membered heterocyclic ring containing at least one heteroatom selected from N, O, and S. Examples of such ring include, but are not limited to, cyclopropyl, cyclobutyl, cyclopentyl, cyclohexyl, tetrahydrofuryl, tetrahydrothienyl, and tetrahydropyranyl, preferably cyclopropyl, cyclobutyl, cyclopentyl, cyclohexyl, and tetrahydropyranyl, and most preferably cyclopropyl, cyclobutyl, cyclopentyl, and tetrahydropyranyl Where $R^b$ and $R^c$ together with the nitrogen atom to which they are attached form a 5 to 6 membered ring, this 5 to 6 membered ring represents 5 to 6 membered heterocyclic ring containing a nitrogen atom and optionally containing one heteroatom selected from N, O, and S. Examples of such ring include, but are not limited to, 1-pyrrolidinyl, 1-imidazolidinyl, 1-pyrazolidinyl, 1-piperidinyl, 1-piperazinyl, 4-morpholinyl and 4-thiomorpholinyl. Of these, 1-pyrrolidinyl, 1-piperidinyl, 4-morpholinyl and 4-thiomorpholinyl are preferred; and 4-morpholinyl is more preferred.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

Preferred classes of compounds of the present invention are those compounds of formula (I) or a pharmaceutically acceptable salt thereof, each as described herein, in which:

(a) A is carbon;

(b) $R^1$ is $C_1$-$C_2$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl;

(c) $R^1$ is $C_1$-$C_2$ alkyl substituted with 1 to 2 substituents independently selected from the group consisting of trifluoromethyl, trifluoromethoxy, cycloalkyl, hydroxy-substituted cycloalkyl, amino-substituted cycloalkyl, heterocyclyl, and alkyl-substituted heterocyclyl;

(d) $R^1$ is $C_1$-$C_2$ alkyl substituted with one substituent selected from the group consisting of isopropyl, trifluoromethyl, trifluoromethoxy, dimethylamino, cyclopropyl, 1-hydroxycyclopentyl, 1-aminocyclopentyl, 2-tetrahydrofuranyl, 4-tetrahydropyranyl, 4-hydroxy-4-tetrahydropyranyl, 1-pyrrolidinyl, 1-piperidinyl, 4-morpholinyl, 1-methyl-2-pyrrolidinyl and 1-methyl-2-piperidinyl;

(e) $R^2$ is alkyl-substituted $C_3$-$C_5$ cycloalkyl, $C_4$-$C_8$ alkyl, alkoxy-substituted $C_4$-$C_8$ alkyl, or methyl substituted with one substituent selected from the group consisting of $C_3$-$C_{10}$ cycloalkyl and alkyl-substituted $C_3$-$C_5$ cycloalkyl;

(f) $R^2$ is tert-butyl, 2,2-dimethylpropyl, 2,2-dimethylbutyl, 2,4,4-trimethylpentyl, 3-methoxy-2,2-dimethylpropyl, 2,2,3,3-tetramethylcyclopropyl, 2,2-dimethylcyclopropyl, cyclopropylmethyl, cyclopentylmethyl, (1-methylcyclopropyl)methyl or (1-methylcyclopentyl)methyl;

(g) $R^2$ is tert-butyl or 2,2-dimethylpropyl;

(h) $R^3$ is —$NR^aCO$—$NR^bR^c$, —$NR^aCO$—($C_1$-$C_4$ alkyl), —$CO$—$NR^bR^c$, —$NR^aSO_2$—$NR^bR^c$ or —$NR^aSO_2$—($C_1$-$C_4$ alkyl), wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy;

(i) $R^3$ is —$NR^aCO$—$NR^bR^c$, —$NR^aCO$—($C_1$-$C_4$ alkyl) or —$CO$—$NR^bR^c$, wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy;

(j) $R^3$ is —$CO$—$NR^bR^c$, wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy;

(k) $R^3$ is —$CONH_2$, —$CONHCH_3$, —$CON(CH_3)_2$, —$CONH(CH_2)_2OH$, —$CONH(CH_2)_2NH_2$, —$CONH(CH_2)_2N(CH_3)_2$, —$CONHCH_2CONH_2$, —$CONHCH_2CON(CH_3)_2$ or —$CONHCH_2COOH$;

(l) $R^4$ and $R^5$ are independently selected from hydrogen or $C_1$-$C_4$ alkyl; or alternatively $R^4$ and $R^5$ together with the carbon atom to which they are attached form a 3 to 6 membered ring;

(m) $R^4$ and $R^5$ are independently selected from hydrogen, methyl, ethyl, propyl or isopropyl; or alternatively $R^4$ and $R^5$ together with the carbon atom to which they are attached form a 3 to 6 membered ring; said 3 to 6 membered ring being selected from the group consisting of cyclopropane, cyclobutane, cyclopentane, cyclohexane, tetrahydrofuran and tetrahydro-2H-pyran;

(n) $R^4$ and $R^5$ are both methyl; or alternatively $R^4$ and $R^5$ together with the carbon atom to which they are attached form a 3 to 6 membered ring; said 3 to 6 membered ring being selected from the group consisting of cyclopropane, cyclobutane, cyclopentane, cyclohexane, tetrahydrofuran and tetrahydro-2H-pyran;

(o) m and n are independently selected from 0 or 1.

Of these classes of compounds, any combination among (a) to (n) is also preferred.

Particularly preferred compounds of the present invention are those compounds of formula (I) or a pharmaceutically acceptable salt thereof in which:

(A) A is carbon; $R^1$ is $C_1$-$C_4$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl; $R^2$ is cycloalkyl, alkyl-substituted cycloalkyl, $C_3$-$C_{10}$ alkyl, alkoxy-substituted $C_3$-$C_{10}$ alkyl or $C_1$-$C_2$ alkyl, said $C_1$-$C_2$ alkyl being substituted with 1 to 2 substituents independently selected from the group consisting of cycloalkyl and alkyl-substituted cycloalkyl; $R^3$ is —$NR^aCO$—$NR^bR^c$, —$NR^aCO$—($C_1$-$C_4$ alkyl), —$CO$—$NR^bR^c$, —$NR^aSO_2$—$NR^bR^c$ or —$NR^aSO_2$—($C_1$-$C_4$ alkyl), wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl) aminocarbonyl or carboxy; or alternatively $R^b$ and $R^c$ together with nitrogen atom to which they are attached form a 5 to 6 membered ring; $R^4$ and $R^5$ are independently selected from the group consisting of hydrogen, halogen, $C_1$-$C_4$ alkyl and $C_1$-$C_4$ alkoxy; or alternatively $R^4$ and $R^5$ together with the carbon atom to which they are attached form a 3 to 6 membered ring; and m and n are independently selected from 0 or 1;

(B) A is carbon or nitrogen; $R^1$ is $C_1$-$C_2$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl; $R^2$ is cycloalkyl, alkyl-substituted cycloalkyl, $C_3$-$C_{10}$ alkyl, alkoxy-substituted $C_3$-$C_{10}$ alkyl or $C_1$-$C_2$ alkyl, said $C_1$-$C_2$ alkyl being substituted with 1 to 2 substituents independently selected from the group consisting of cycloalkyl and alkyl-substituted cycloalkyl; $R^3$ is —$NR^aCO$—$NR^bR^c$, —$NR^aCO$—($C_1$-$C_4$ alkyl), —$CO$—$NR^bR^c$, —$NR^aSO_2$—$NR^bR^c$ or —$NR^aSO_2$—($C_1$-$C_4$ alkyl), wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl) aminocarbonyl or carboxy; or alternatively $R^b$ and $R^c$ together with nitrogen atom to which they are attached form a 5 to 6 membered ring; $R^4$ and $R^5$ are independently selected from the group consisting of hydrogen, halogen, $C_1$-$C_4$ alkyl and $C_1$-$C_4$ alkoxy; or alternatively $R^4$ and $R^5$ together with the carbon atom to which they are attached form a 3 to 6 membered ring; and m and n are independently selected from 0 or 1;

(C) A is carbon or nitrogen; $R^1$ is $C_1$-$C_2$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl; $R^2$ is alkyl-substituted $C_3$-$C_5$ cycloalkyl, $C_4$-$C_8$ alkyl, alkoxy-substituted $C_4$-$C_8$ alkyl, or methyl substituted with one substituent selected from the group consisting of $C_3$-$C_5$ cycloalkyl and alkyl-substituted $C_3$-$C_5$ cycloalkyl; $R^3$ is —$NR^aCO$—$NR^bR^c$, —$NR^aCO$—($C_1$-$C_4$ alkyl), —$CO$—$NR^bR^c$, —$NR^aSO_2$—$NR^bR^c$ or —$NR^aSO_2$—($C_1$-$C_4$ alkyl), wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; or alternatively $R^b$ and $R^c$ together with nitrogen atom to which they are attached form a 5 to 6 membered ring; $R^4$ and $R^5$ are independently selected from the group consisting of hydrogen, halogen, $C_1$-$C_4$ alkyl and $C_1$-$C_4$ alkoxy; or alternatively $R^4$ and $R^5$ together with the carbon atom to which they are attached form a 3 to 6 membered ring; and m and n are independently selected from 0 or 1;

(D) A is carbon or nitrogen; $R^1$ is $C_1$-$C_2$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl; $R^2$ is alkyl-substituted $C_3$-$C_6$ cycloalkyl, $C_4$-$C_8$ alkyl, alkoxy-substituted $C_4$-$C_8$ alkyl, or methyl substituted with one substituent selected from the group consisting of $C_3$-$C_5$ cycloalkyl and alkyl-substituted $C_3$-$C_5$ cycloalkyl; $R^3$ is —$NR^aCO$—$NR^bR^c$, —$NR^aO$—($C_1$-$C_4$ alkyl), —$CO$—$NR^bR^c$, —$NR^aSO_2$—$NR^bR^c$ or —$NR^aSO_2$—($C_1$-$C_4$ alkyl), wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; $R^4$ and $R^5$ are independently selected from the group consisting of hydrogen, halogen, $C_1$-$C_4$ alkyl and $C_1$-$C_4$ alkoxy; or alternatively $R^4$ and $R^5$ together with the carbon atom to which they are attached form a 3 to 6 membered ring; and m and n are independently selected from 0 or 1;

(E) A is carbon or nitrogen; $R^1$ is $C_1$-$C_2$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl; $R^2$ is alkyl-substituted $C_3$-$C_6$ cycloalkyl, $C_4$-$C_8$ alkyl, alkoxy-substituted $C_4$-$C_8$ alkyl, or methyl substituted with one substituent selected from the group consisting of $C_3$-$C_5$ cycloalkyl and alkyl-substituted $C_3$-$C_5$ cycloalkyl; $R^3$ is —$NR^aCO$—$NR^bR^c$, —$NR^aCO$—($C_1$-$C_4$ alkyl), —$CO$—$NR^bR^c$, —$NR^aSO_2$—$NR^bR^c$ or —$NR^aSO_2$—($C_1$-$C_4$ alkyl), wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; or alternatively $R^b$ and $R^c$ together with nitrogen atom to which they are attached form a 5 to 6 membered ring; $R^4$ and $R^5$ are independently selected from hydrogen or $C_1$-$C_4$ alkyl; or alternatively $R^4$ and $R^5$ together with the carbon atom to which they are attached form a 3 to 6 membered ring; and m and n are independently selected from 0 or 1;

(F) A is carbon or nitrogen; $R^1$ is $C_1$-$C_2$ alkyl substituted with 1 to 2 substituents independently selected from the group consisting of $C_1$-$C_4$ alkyl, hydroxy, trifluoromethyl, trifluoromethoxy, $C_1$-$C_4$ alkoxy, amino, $C_1$-$C_4$ alkylamino, di($C_1$-$C_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl; $R^2$ is alkyl-substituted $C_3$-$C_6$ cycloalkyl, $C_4$-$C_8$ alkyl, alkoxy-substituted $C_4$-$C_8$ alkyl, or methyl substituted with one substituent selected from the group consisting of $C_3$-$C_5$ cycloalkyl and alkyl-substituted $C_3$-$C_5$ cycloalkyl; $R^3$ is —$NR^aCO$—$NR^bR^c$, —$NR^aCO$—($C_1$-$C_4$ alkyl), —$CO$—$NR^bR^c$, —$NR^aSO_2$—$NR^bR^c$ or —$NR^aSO_2$—($C_1$-$C_4$ alkyl), wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; $R^4$ and $R^5$ are independently selected from hydrogen or $C_1$-$C_4$ alkyl; or alternatively $R^4$ and $R^5$ together with the carbon atom to which they are attached form a 3 to 6 membered ring; and m and n are independently selected from 0 or 1;

(G) A is carbon or nitrogen; $R^1$ is $C_1$-$C_2$ alkyl substituted with 1 to 2 substituents independently selected from the group consisting of trifluoromethyl, trifluoromethoxy, cycloalkyl, hydroxy-substituted cycloalkyl, amino-substituted cycloalkyl, heterocyclyl, and alkyl-substituted heterocyclyl; $R^2$ is tert-butyl, 2,2-dimethylpropyl, 2,2-dimethylbutyl, 2,4,4-trimethylpentyl, 3-methoxy-2,2-dimethylpropyl, 2,2,3,3-tetramethylcyclopropyl, 2,2-dimethylcyclopropyl, cyclopropylmethyl, cyclopentylmethyl, (1-methylcyclopropyl)methyl or (1-methylcyclopentyl)methyl; $R^3$ is —$CO$—$NR^bR^c$, wherein $R^a$, $R^b$ and $R^c$ are independently selected from hydrogen or $C_1$-$C_4$ alkyl, said $C_1$-$C_4$ alkyl optionally substituted with hydroxy, amino, $C_1$-$C_4$ alkylamino, di($C_1$-$C_4$ alkyl)amino, aminocarbonyl, $C_1$-$C_4$ alkylaminocarbonyl, di($C_1$-$C_4$ alkyl)aminocarbonyl or carboxy; $R^4$ and $R^5$ are independently selected from hydrogen or $C_1$-$C_4$ alkyl; or alternatively $R^4$ and $R^5$ together with the carbon atom to which they are attached form a 3 to 6 membered ring; and m and n are independently selected from 0 or 1;

(H) A is carbon or nitrogen; $R^1$ is $C_1$-$C_2$ alkyl substituted with one substituent selected from the group consisting of isopropyl, trifluoromethyl, trifluoromethoxy, dimethylamino, cyclopropyl, 1-hydroxycyclopentyl, 1-aminocyclopentyl, 2-tetrahydrofuranyl, 4-tetrahydropyranyl, 4-hydroxy-4-tetrahydropyranyl, 1-pyrrolidinyl, 1-piperidinyl, 4-morpholinyl, 1-methyl-2-pyrrolidinyl and 1-methyl-2-piperidinyl; $R^2$ is a tert-butyl group or 2,2-dimethylpropyl group; $R^3$ is —$CONH_2$, —$CONHCH_3$, —$CON(CH_3)_2$, —$CONH(CH_2)_2OH$, —$CONH(CH_2)_2NH_2$, —$CONH$ —(CH$_2$)$_2$N(CH$_3$)$_2$, —CONHCH$_2$CONH$_2$, —CONHCH$_2$CON(CH$_3$)$_2$, —CONHCH$_2$COOH, —NHSO$_2$NH$_2$, —NHSO$_2$NHCH$_3$, —NHSO$_2$N(CH$_3$)$_2$ or —NHSO$_2$CH$_3$; R$^4$ and R$^5$ are independently selected from hydrogen, methyl, ethyl, propyl or isopropyl; or alternatively R$^4$ and R$^5$ together with the carbon atom to which they are attached form a 3 to 6 membered ring; said 3 to 6 membered ring being selected from the group consisting of cyclopropane, cyclobutane, cyclopentane, cyclohexane, tetrahydrofuran and tetrahydro-2H-pyran; and m and n are independently selected from 0 or 1;

(I) A is carbon or nitrogen; R$^1$ is C$_1$-C$_2$ alkyl substituted with one substituent selected from the group consisting of isopropyl, trifluoromethyl, trifluoromethoxy, dimethylamino, cyclopropyl, 1-hydroxycyclopentyl, 1-aminocyclopentyl, 2-tetrahydrofuranyl, 4-tetrahydropyranyl, 4-hydroxy-4-tetrahydropyranyl, 1-pyrrolidinyl, 1-piperidinyl, 4-morpholinyl, 1-methyl-2-pyrrolidinyl and 1-methyl-2-piperidinyl; R$^2$ is a tert-butyl group or 2,2-dimethylpropyl group; R$^3$ is —CONH$_2$, —CONHCH$_3$, —CON(CH$_3$)$_2$, —CONH(CH$_2$)$_2$OH, —CONH(CH$_2$)$_2$NH$_2$, —CONH(CH$_2$)$_2$N(CH$_3$)$_2$, —CONHCH$_2$CONH$_2$, —CONHCH$_2$CON(CH$_3$)$_2$, —CONHCH$_2$COOH, —NHSO$_2$NH$_2$, —NHSO$_2$NHCH$_3$, —NHSO$_2$N(CH$_3$)$_2$ or —NHSO$_2$CH$_3$; R$^4$ and R$^5$ are both methyl; or alternatively R$^4$ and R$^5$ together with the carbon atom to which they are attached form a 3 to 6 membered ring; said 3 to 6 membered ring being selected from the group consisting of cyclopropane, cyclobutane, cyclopentane, cyclohexane, tetrahydrofuran and tetrahydro-2H-pyran; and m and n are independently selected from 0 or 1.

One embodiment of the invention provides a compound selected from the group consisting of:

2-{[1-(Cyclopropylmethyl)-2-(2,2-dimethylpropyl)-1H-benzimidazol-5-yl]sulfonyl}-2-methylpropanamide;

1-{[1-(Cyclopropylmethyl)-2-(2,2-dimethylpropyl)-1H-benzimidazol-5-yl]sulfonyl}cyclopropanecarboxamide;

1-{[1-(Cyclopropylmethyl)-2-(2,2-dimethylpropyl)-1H-benzimidazol-5-yl]sulfonyl}cyclobutanecarboxamide;

4-{[1-(Cyclopropylmethyl)-2-(2,2-dimethylpropyl)-1H-benzimidazol-5-yl]sulfonyl}tetrahydro-2H-pyran-4-carboxamide; and 2-{[3-(Cyclopropylmethyl)-2-(2,2-dimethylpropyl)-3H-imidazo[4,5-b]pyridin-6-yl]sulfonyl}-2-methylpropanamide;

or a pharmaceutically acceptable salt thereof.

One embodiment of the invention provides a compound selected from the group consisting of:

2-{[1-(Cyclopropylmethyl)-2-(2,2-dimethylpropyl)-1H-benzimidazol-5-yl]sulfonyl}-N,N,2-trimethylpropanamide;

2-{[1-(Cyclopropylmethyl)-2-(2,2-dimethylpropyl)-1H-benzimidazol-5-yl]sulfonyl}-N-(2-hydroxyethyl)-2-methylpropanamide;

N-(2-{[1-(Cyclopropylmethyl)-2-(2,2-dimethylpropyl)-1H-benzimidazol-5-yl]sulfonyl}-2-methylpropyl)methanesulfonamide;

N-(2-{[1-(cyclopropylmethyl)-2-(2,2-dimethylpropyl)-1H-benzimidazol-5-yl]sulfonyl}-2-methylpropyl)-N'-methylurea; and N-(2-{[1-(cyclopropylmethyl)-2-(2,2-dimethylpropyl)-1H-benzimidazol-5-yl]sulfonyl}-2-methylpropyl)urea;

or a pharmaceutically acceptable salt thereof.

Pharmaceutically acceptable salts of a compound of formula (I) include the acid addition (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising a compound of the invention and one or more pharmaceutically acceptable solvent molecules, for example, ethanol. The term 'hydrate' is employed when said solvent is water.

Pharmaceutically acceptable solvates in accordance with the invention include hydrates and solvates wherein the solvent of crystallization may be isotopically substituted, e.g. D$_2$O, d$_6$-acetone, d$_6$-DMSO.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see *J Pharm Sci*, 64 (8), 1269-1288 by Haleblian (August 1975).

Hereinafter all references to a compound of formula (I) include references to salts and complexes thereof and to solvates and complexes of salts thereof.

The term "compound of the invention" or "compounds of the invention" refers to, unless indicated otherwise, a compound of formula (I) as hereinbefore defined, polymorphs, prodrugs, and isomers thereof (including optical, geometric and tautomeric isomers) as hereinafter defined and isotopically-labeled compounds of formula (I).

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985). Some examples of prodrugs in accordance with the invention include:
(i) where the compound of formula (I) contains an alcohol functionality (—OH), an ether thereof, for example, replacement of the hydrogen with $(C_1-C_6)$alkanoyloxymethyl; and
(ii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition salts wherein the counterion is optically active, for example, D-lactate or L-lysine, or racemic, for example, DL-tartrate or DL-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labeled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

All of the compounds of the formula (I) can be prepared by the procedures described in the general methods presented below or by the specific methods described in the Examples section and the Preparations section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Methods A to E.

The following Methods A and C illustrate the preparation of compounds of formula (I).

Unless otherwise indicated, $R^1$, $R^2$, $R^3$, $R^4$, $R^6$, A, m and n in the following Methods are as defined above. The term "protecting group", as used hereinafter, means a hydroxy, carboxy or amino-protecting group. Typical hydroxy, carboxy or amino-protecting groups are described in *Protective Groups in Organic Synthesis* edited by T. W. Greene er al. (John Wiley & Sons, 1999). All starting materials in the following general syntheses may be commercially available or obtained by conventional methods known to those skilled in the art, such as *Journal of Organic Chemistry*, 48(4), 604-5; 1983, *Canadian Journal of Chemistry*, 62(8), 1544-7; 1984, *Chemical & Environmental Research*, 11(1 & 2), 63-75; 2002, and *Chemical & Pharmaceutical Bulletin*, 38(10), 2853-8; 1990, the disclosures of which are incorporated herein by reference.

Method A

This illustrates the preparation of compounds of formula (I) wherein $R^3$ is —CO—$NR^bR^c$.

Reaction scheme A

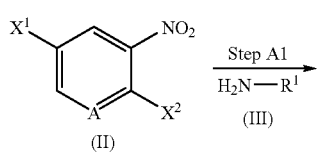

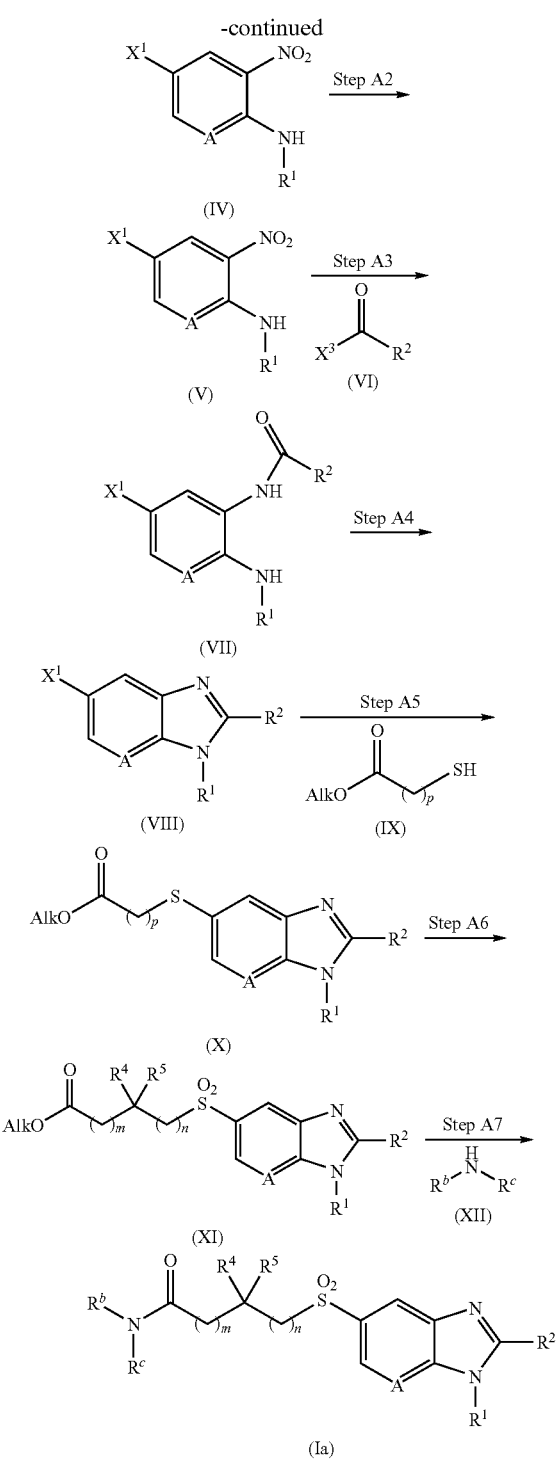

(III) are commercially available or can be obtained by conventional methods known to those skilled in the art.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: amides, such as formamide, N,N-dimethylformamide, N,N-dimethylacetamide and hexamethylphosphoric triamide; alcohols, such as methanol, ethanol, propanol, 2-propanol and butanol; nitrites, such as acetonitrile and benzonitrile; and sulfoxides, such as dimethyl sulfoxide and sulfolane. Of these solvents, alcohols are preferred; ethanol is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

In this reaction, microwave can be employed to accelerate the reaction. In the case of employing microwave, the reaction at a temperature may be from about 0° C. to about 160° C. and the reaction time from about 5 minutes to about 12 hours will usually suffice.

Step A2

In this step, the compound of formula (V) is prepared by reduction of the nitro group of the compound of formula (IV).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aromatic hydrocarbons, such as benzene and toluene; alcohols, such as methanol, ethanol, propanol, 2-propanol and butanol; and esters, such as ethyl acetate. Of these solvents, methanol and ethanol are preferred.

The reaction is carried out in the presence of a reducing agent. There is likewise no particular restriction on the nature of the reducing agents used, and any reducing agent commonly used in reactions of this type may equally be used here. Examples of such reducing agents include, a combination of hydrogen gas and a catalyst such as palladium-carbon, platinum on sulfide carbon and Raney nickel; a combination of iron and ammoniumchloride and a combination of zinc and hydrochloric acid. In the case of employing platinum on sulfide carbon, the pressure of hydrogen gas preferably range from about 1 atom to about 4 atom. Of these, a combination of iron and ammoniumchloride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected In Reaction Scheme A, A, $R^1$, $R^2$, $R^4$, $R^5$, $R^b$, $R^c$, m and n are as defined above. $X^1$, $X^2$ and $X^3$ are a halogen atom, preferably bromine or iodine for $X^1$, fluorine or chlorine for $X^2$, and chlorine for $X^3$. p is equal to m+n+1. Alk is $C_1$-$C_4$ alkyl, preferably methyl.

Step A1

In this step, the compound of formula (IV) is prepared by reaction of the compound of formula (II) with the compound of formula (III). Both compounds of formula (II) and formula under the preferred conditions outlined above, a period of from about 5 minutes to about 24 hours will usually suffice.

Step A3

In this step, the compound of formula (VII) is prepared by amidation of the compound of formula (V) with the compound of formula (VI), which is commercially available.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; amides, such as formamide, N,N-dimethylformamide, N,N-dimethylacetamide and hexamethylphosphoric triamide; nitrites, such as acetonitrile and benzonitrile; and esters, such as ethyl acetate and methyl acetate. Of these solvents, esters are preferred; ethyl acetate is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step A4

In this step, the desired compound of formula (VIII) is prepared by the cyclization of the compound of formula (VII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aromatic hydrocarbons, such as benzene, toluene and nitrobenzene; amides, such as formamide, N,N-dimethylformamide, N,N-dimethylacetamide and hexamethylphosphoric triamide; alcohols, such as methanol, ethanol, propanol, 2-propanol and butanol; nitrites, such as acetonitrile and benzonitrile; and esters, such as ethyl acetate and methyl acetate. Of these solvents, alcohols and aromatic hydrocarbons are preferred; methanol, ethanol, propanol, 2-propanol, butanol and toluene are more preferred.

The reaction is carried out in the presence of an acid or base. There is likewise no particular restriction on the nature of the acids or bases used, and any ones commonly used in reactions of this type may equally be used here. Examples of such acids or bases include: acids, such as hydrochloric acid, sulfuric acid, or p-toluenesulfonic acid; and alkali metal hydroxides, such as lithium hydroxide, sodium hydroxide and potassium hydroxide. Of these, p-toluenesulfonic acid and sodium hydroxide are preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

In this reaction, microwave can be employed to accelerate the reaction. In the case of employing microwave, the reaction at a temperature may be from about 0° C. to about 130° C. and the reaction time from about 5 minutes to about 12 hours will usually suffice.

Step A5

In this step, the desired compound of formula (X) is prepared by coupling reaction of the compound of formula (VIII) with the compound of formula (IX) under the presence of palladium catalyst. The compound of formula (IX) is commercially available or can be obtained by conventional methods known to those skilled in the art.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylaniline; alcohols, such as methanol, ethanol, propanol, 2-propanol and butanol; nitrites, such as acetonitrile and benzonitrile; sulfoxides, such as dimethyl sulfoxide and sulfolane; ketones, such as acetone and diethylketone. Of these solvents, ethers are preferred; dioxane is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step A6

In this step, the desired compound of formula (XI) is prepared by oxidation of the compound of formula (X) followed by alkylation.

Oxidation

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; and aromatic hydrocarbons, such as benzene, toluene and nitrobenzene. Of these solvents, halogenated hydrocarbons are preferred; dichloromethane is more preferred.

The reaction is carried out in the presence of an oxidizing agent. There is likewise no particular restriction on the nature of the oxidizing agents used, and any oxidizing agent commonly used in reactions of this type may equally be used here. Examples of such oxidizing agents include: high valence iodine oxidizing agents, such as $NaIO_4$ or 1,1,1-triacetoxy-1,1-dihydro-1,2-benziodoxol-3(1H)-one (Dess-Martin periodinane); or peracids, such as $H_2O_2$, $CH_3COOOH$ or m-chloroperbenzoic acid (mCPBA). Of these, mCPBA is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Alkylation

Optionally, alkylation can be conducted in step A6 to introduce $R^4$ and $R^5$, using the compound of $R^4$—X and/or $R^5$—X, or X—$(CH_2)_q$—Q—$(CH_2)_r$—X, wherein X is halogen, Q is carbon or oxygen, q and r are independently 0, 1 or 2 with the proviso that q plus r is 1, 2, 3 or 4.

This reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diiropropyl amide, potassium diisopropyl amide, sodium diiropropyl amide, lithium bis(trimethylsilyl)amide and potassium bis(trimethylsilyl)amide. Of these, alkali metal hydrides are preferred. Sodium hydride is preferred.

This reaction is normally and preferably effected in the presence of solvent. There is no particular restriction on the nature of the solvent to be employed, provided that it has no adverse effect on the reaction or the reagents involved and that H can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, tetrahydrofuran (THF), and dioxane; aromatic hydrocarbons, such as benzene, toluene and nitrobenzene; amides, such as, N,N-dimethylformamide (DMF), N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; nitriles, such as acetonitrile and benzonitrile; sulfoxides, such as dimethyl sulfoxide (DMSO) and sulfolane; ketones, such as acetone and diethylketone. Of these solvents, amides are preferred and DMF is more preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 150° C., more preferably from about 0° C. to about 70° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours.

Step A7

In this step, the desired compound of formula (Ia) is prepared by ester hydrolysis of the compound of formula (XI) followed by amidation with the compound of formula (XII).

Ester Hydrolysis

The ester hydrolysis is normally and preferably effected in the presence of solvent. There is no particular restriction on the nature of the solvent to be employed, provided that it has no adverse, effect on the reaction or the reagents involved and that it can dissolve reagents, at least to some extent. Examples of suitable solvents include, but are not limited to: ethers, such as diethyl ether, diisopropyl ether, tetrahydrofuran (THF), and dioxane, and alcohols such as methanol, ethanol, propanol, isopropanol, and butanol. Of these solvents, THF and methanol are preferred.

The ester hydrolysis is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide. Of these, sodium hydroxide and potassium hydroxide are preferred.

The ester hydrolysis can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 120° C., more preferably from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 48 hours.

Amidation

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: amides, such as formamide, N,N-dimethylformamide, N,N-dimethylacetamide and hexamethylphosphoric triamide; nitriles, such as acetonitrile and benzonitrile; and esters, such as ethyl acetate and methyl acetate. Of these solvents, nitriles are preferred; acetonitrile is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Method B

This illustrates the preparation of compounds of formula (Ib).

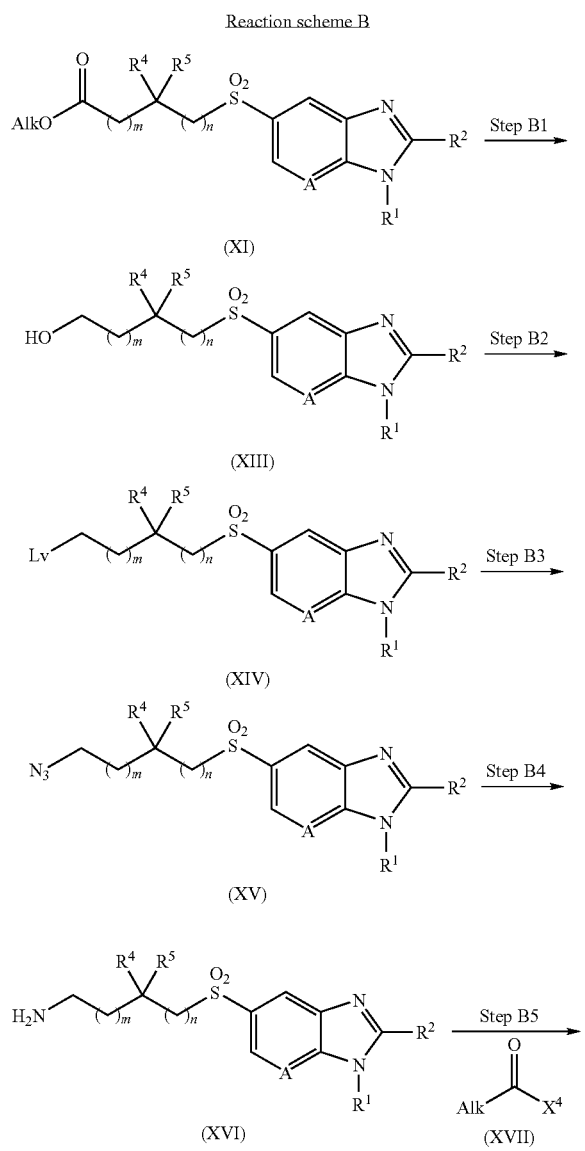

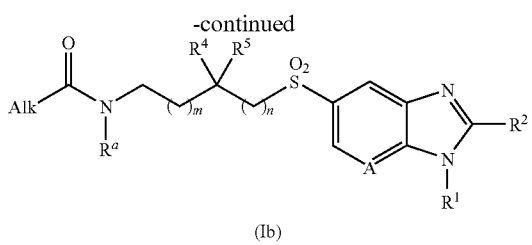

In Reaction Scheme B, A, $R^1$, $R^2$, $R^4$, $R^5$, $R^a$, m and n are as defined above. $X^4$ is a halogen atom, preferably chlorine. Lv is a leaving group. Alk is $C_1$-$C_4$ alkyl, preferably methyl.

The term "leaving group", as used herein, signifies a group capable of being substituted by nucleophilic groups, such as a hydroxy group, amines or carboanions and examples of such leaving groups include halogen atoms, a alkylsulfonyl group and an arylsulfonyl group. Of these, a chlorine atom, a methylsulfonyl group, a trifluoromethylsulfonyl group and 4-methylphenylsulfonyl group are preferred.

Step B1

In this step, the compound of formula (XIII) is prepared by ester reduction of the compound of formula (XI), which can be prepared as described in Step A6.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; ethers, such as diethyl ether, diisopropyl ether, tetrahydrofuran and dioxane; and aromatic hydrocarbons, such as benzene, toluene and nitrobenzene. Of these solvents, tetrahydrofuran is preferred.

The reaction is carried out in the presence of a reducing agent. There is likewise no particular restriction on the nature of the reducing agents used, and any reducing agent commonly used in reactions of this type may equally be used here. Examples of such reducing agents include: borane reagents, such as boran-tetrahydrofuran complex, boran-dimethyl sulfide complex (BMS) and 9-borabicyclo[3,3,1]nonane (9-BBN); and hydride compounds such as lithium aluminum hydride and diisobutyl aluminum hydride. Of these, lithium aluminum hydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step B2

In this step, the compound of formula (XIV) is prepared by nucleophilic substitution.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; and sulfoxides, such as dimethyl sulfoxide and sulfolane. Of these solvents, amides are preferred; N,N-dimethylformamide is more preferred.

This reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diiropropyl amide, potassium diisopropyl amide, sodium diiropropyl amide, lithium bis(trimethylsilyl)amide and potassium bis(trimethylsilyl)amide. Of these, amines are preferred; triethylamine is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step B3

In this step, the compound of formula (XV) is prepared by nucleophilic substitution of the compound of formula (XIV) with azide such as sodium azide.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone. Of these solvents, amides are preferred; N,N-dimethylformamide is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step B4

In this step, the compound of formula (XVI) is prepared by azide reduction of the compound of formula (XV).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylaniline; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone. Of these solvents, alcohols are preferred; methanol is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step B5

In this step, the compound of formula (Ib) is prepared by amidation of the compound of formula (XVI) with the compound of formula (XVII) using the similar condition described in Step A3.

Optionally, $R^a$ may be introduced by alkylation, which is well known by the skilled in the art.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylaniline; alcohols, such as methanol, ethanol, propanol, 2-propanol and butanol; nitrites, such as acetonitrile and benzonitrile; sulfoxides, such as dimethyl sulfoxide and sulfolane; ketones, such as acetone and diethylketone. Of these solvents, halogenated hydrocarbons are preferred; dichloromethane is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Method C

This illustrates the preparation of compounds of formula (Ic).

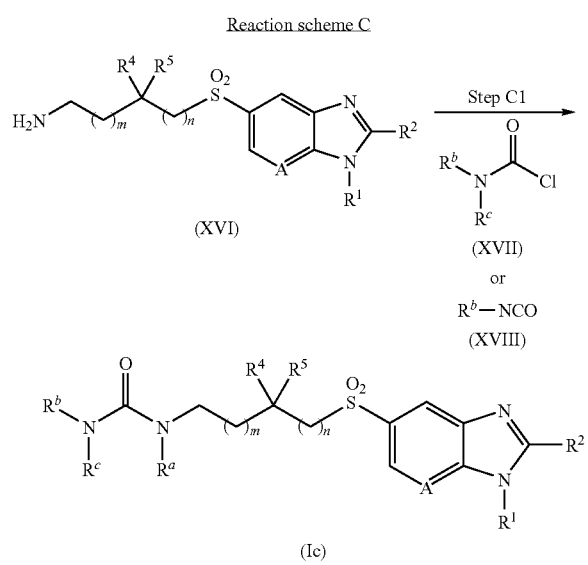

In Reaction Scheme C, A, $R^1$, $R^2$, $R^4$, $R^5$, $R^a$, $R^b$, $R^c$, m and n are as defined above.

Step C1

In this step, the compound of formula (Ic) is prepared by coupling reaction of the compound of formula (XVI), which can be prepared as described in Step B4 with the compound of formula (XVII) or the compound of formula (XVIII), both of which are commercially available or obtained by conventional methods known to those skilled in the art.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylaniline; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone. Of these solvents, halogenated hydrocarbons are preferred; dichloromethane is more preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

The compounds of formula (I), and the intermediates above-mentioned preparation methods can be isolated and purified by conventional procedures, such as distillation, recrystallization or chromatographic purification.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients. The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colorants, flavoring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

The formulation of tablets is discussed in "*Pharmaceutical Dosage Forms: Tablets, Vol. 1*", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, *Pharmaceutical Technology On-line*, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J Pharm Sci*, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as i-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from about 1 µg to about 20 mg of the compound of the invention per actuation and the actuation volume may vary from about 1 µl to about 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, poly(DL-lacticcoglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from about 1 to about 100 µg of the compound of formula (I). The overall daily dose will typically be in the range about 50 µg to about 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in WO 91/11172, WO 94/02518 and WO 98/55148.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 100 mg depending, of course, on the mode of administration, preferred in the range of about 0.1 mg to about 50 mg and more preferred in the range of about 0.5 mg to about 20 mg. For example, oral administration may require a total daily dose of from about 1 mg to about 20 mg, while an intravenous dose may only require from about 0.5 mg to about 10 mg. The total daily dose may be administered in single or divided doses.

These dosages are based on an average human subject having a weight of about 65 kg to about 70 kg. The physician will readily be able to determine doses for subjects whose weight falls outside this range, such as infants and the elderly.

As discussed above, a compound of the invention exhibits CB2 agonist activity. A CB2 agonist of the present invention may be usefully combined with another pharmacologically active compound, or with two or more other pharmacologically active compounds, particularly in the treatment of the cancer, inflammatory diseases, immunomodulatory diseases and gastrointestinal disorder. For example, a CB2 agonist, particularly a compound of the formula (I), or a pharmaceutically acceptable salt thereof, as defined above, may be administered simultaneously, sequentially or separately in combination with one or more agents selected from:

(i) 5-HT$_3$ antagonists, e.g. dolasetron, palonosetron, alosetron, azasetron and ramosetron, mitrazapine, granisetron, tropisetron, E-3620, ondansetron and indisetron;

(ii) 5-HT$_4$ agonists, e.g. tegaserod, mosapride, cinitapride and oxtriptane;

(iii) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine Modulon® (trimebutine malate), Imodium® (loperamide) and pentazocine;

(iv) tricyclic antidepressants, e.g. imipramine, amitriptyline, clomipramine, amoxapine and lofepramine;

(v) somatostatin analogues, e.g. octreotide, AN-238 and PTR-3173;

(vi) anticholinergics, e.g. dicyclomine and hyoscyamine, ipratropium bromide, ipratropium, tiotropium bromide;

(vii) laxatives, e.g. Trifyba®, Fybogel®, Konsyl®, Isogel®, Regulan®, Celevac® and Normacol®;

(viii) fiber products, e.g. Metamucil®;

(ix) antispasmodics, e.g.: mebeverine;

(x) dopamine antagonists, e.g. metoclopramide, domperidone and levosulpiride;

(xi) cholinergics, e.g. neostigmine, pilocarpine, carbachol (xii) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and tasudil;

(xiii) Cl Channel activator: e.g. lubiprostone;

(xiv) selective serotonin reuptake inhibitors, e.g. sertraline, escitalopram, fluoxetine, nefazodone, fluvoxamine, citalopram, milnacipran, paroxetine, venlafaxine, tramadol, sibutramine, duloxetine, desvenlafaxine and depoxetine;

(xv) GABA agonists, e.g. gabapentin, topiramate, cinolazepam, clonazopam, progabide, brotizolam, zopiclone, pregabalin and eszopiclone;

(xvi) tachykinin (NK) antagonists, particularly NK-3, NK-2 and NK-1 antagonists, e.g.: nepadutant, saredutant, talnetant, (αR,9R)-7-[3,5-bis(trifluoromethyl)benzyl]-8,9,10, 11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl] ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl] methylamino]-2-phenyl-piperidine (2S,3S).

(xvii) α2 agonists, e.g. clonidine, medetomidine, lofexidine, moxonidine, tizanidine, guanfacine, guanabenz, talipexole and dexmedetomidine;

(xviii) benzodiazepine agonists, e.g. diazepam, zaleplon, zolpidem, haloxazolam, clonazepam, prazepam, quazepam, flutazolam, triazolam, lormetazepam, midazolam, tofisopam, clobazam, flunitrazepam and flutoprazepam;

(xix) prostaglandin analogues, e.g. Prostaglandin, misoprostol, treprostinil, esoprostenol, latanoprost, iloprost, beraprost, enprostil, ibudilast and ozagrel;

(xx) histamine H$_3$ agonists, e.g. R-alpha-methylhistamine and BP-294;

(xxi) anti-gastric agents, e.g. Anti-gastrin vaccine, itriglumide and Z-360;

(xxii) disease modifying anti-rheumatic drugs (DMARDs), e.g. methotrexate, leflunomide, penicillamine aurothiopropanol sulfonate, sulfasalazine, mesalamine, olsalazine, balsalazide, Hylan G-F 20, glucosamine, chondroitin sulfate, hydroxychloroquine and diacerein.

(xxiii) Tumor Necrosis Factor-Alpha (TNF-α) modulators, e.g. etanercept, infliximab, adalimumab, CDP-870, pegsunercept, ISIS-104838, RDP-58 and thalidomide;

(xxiv) interleukin-based therapies, e.g. anakinra, atlizumab, RGN-303, denileukindiftitox, ilodecakin, oprelvokin and mepolizumab;

(xxv) nonsteroidal antiinflammatory drugs (NSAIDs), e.g. piroxicam, naproxen, indomethacin, ibuprofen, diclofenac, ketorolac, flurbiprofen, aspirin, diflusinal, etodolac, fenbufen, fenoprofen, flufenisal, ketoprofen, meclofenamic acid, mefenamic acid, nabumetone, oxaprozin, phenylbutazone, sulindac, tolmetin and zomepirac;

(xxvi) selective COX-2 inhibitors, e.g. celecoxib, rofecoxib, valdecoxib, etoricoxib, lumiracoxib and LAS-34475;

(xxvii) Centrally Acting Analgesics, e.g. tramadol and oxymorphone ER;

(xxviii) immunosuppressives, e.g. cyclosporine, tacrolimus, rapamycin, azathioprine and mycophenolate mofetil;

(xxix) Multiple Sclerosis (MS) treatments, e.g. interferonβ-1b, interferonβ-1a, glatiramer acetate, mitoxantrone, cyclophosphamide, MBP-8298, AG-284, tiplimotide, BX-471, E-2007, recombinant glial growth factor-2 and natalizumab;

(xxx) Monoclonal Antibodies, e.g. natalizumab, daclizumab, alemtuzumab, omalizumab, TNX-100 and SGN-40;

(xxxi) insulin secretagogues, e.g. glyburide, glipizide, repaglinide and glimiperide;
(xxxii) biguanides, e.g. metformin;
(xxxiii) alpha-glucosidase inhibitors, e.g. acarbose, voglibose and miglitol;
(xxxiv) PPAR γ agonists, e.g. ploglitazone and rosiglitazone;
(xxxv) antibiotics, e.g. sulfacetamide, erythromycin, gentamicin, tobramycin, ciprofloxacin and ofloxacin
(xxxvi) cell adhesion molecule inhibitors, e.g. alicaforsen, MLN-02, alefacept, efalizumab, R-411 and IVL-745;
(xxxvii) anti-allergy drugs, e.g. levocabastine, olopatadine, cromolyn, lodoxamide, pheniramine, ketotifen, mizolastine and epinastine;
(xxxviii) ophthalmologic anti-virals, e.g. adenine arabinoside and idoxuridine;
(xxxix) glaucoma treatments, e.g. timolol, metipranolol, carteolol, betaxolol, levobunolol, brimonidine, iopidine, dorzolamide, epinephrine and dipivefrin;
(xl) alkylating anti-tumor agents, e.g. busulfan, carboplatin, chlorambucil, cisplatin, cyclophosphamide, dacarbazine, ifosfamide, mechlorethamine, melphalan, procarbazine, thiotepa, and uracil mustard;
(xli) nitrosoureas, e.g. carmustine, lumustine and streptozocin;
(xlii) antimetabolites, e.g. 5-fluorouracil, 6-mercaptopurine, capecitabine, cytosine arabinoside, floxuridine, fludarabine, gemcitabine, methotrexate, thioguanine and azathioprine;
(xliii) antitumor biotics, e.g. dactinomycin, daunorubicin, doxorubicin, idarubicin, mitomycin-C, and mitoxantrone;
(xliv) anti-microtubule agents, e.g. vinblastine, vincristine, vindesine, vinorelbine, paclitaxel and docetaxel;
(xlv), vitamine derivatives, e.g., calcipotriol and tacalcitol;
(xlvi) leukotriene antagonists, e.g. montelukast, zafirlukast and pranlukast;
(xlvii) β2 Agonists, e.g. albuterol, levalbuterol, salmeterol, formotero and arformoterol;
(xlviii) corticosteroids, e.g. prednisone, ciclesonide, budesonide, fluticasone, methylprednisolone, hydrocortisone and BP-1011;
(xlix) methylxanthines, e.g. theophylline, aminophylline and doxofylline;
(l) asthma and/or COPD treatments, e.g. roflumilast, tiotropium, israpafant, N-acetylcysteine and α1-antitrypsin;
(li) a vanilloid receptor agonist (e.g. resinferatoxin) or antagonist (e.g. capsazepine);
(lii) an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid; and
(liii) a prostaglandin $E_2$ subtype 4 (EP4) antagonist such as N-[((2-[4-(2-ethyl-4,6-dimethyl-1H-imidazo[4,5-c]pyridin-1-yl)phenyl]ethyl)amino)-carbonyl]-4-methylbenzenesulfonamide or 4-[(1S)-1-({[5-chloro-2-(3-fluorophenoxy)pyridin-3-yl]carbonyl}amino)ethyl]benzoic acid.

Method for Assessing Biological Activities:

The CB2 receptor binding affinity and other biological activities of the compounds of this invention are determined by the following procedures.

Rat CB2 Binding

Rat spleen cells were placed in tissue preparation buffer [5 mM Tris-HCl (pH7.4 at 25° C.) and 2 mM EDTA] and homogenized using a hand held Polytron PT1200CL disruptor set at 25,000 rpm for 30 seconds on ice, then kept on ice for 15 min. The homogenates were centrifuged at 1,000×g at 4° C. for 10 min. The supernatant was recovered and centrifuged at 40,000×g at 4° C. for 10 min. The pellets were then resuspended in 50 mM Tris-HCl (pH7.4 at 25° C.). This suspension was centrifuged once more in the same manner. The final pellet was resuspended in TME buffer (25 mM Tris-HCl (pH7.4), 5 mM $MgCl_2$, 1 mM EDTA, 0.5% BSA), aliquoted and stored at −80° C. until assayed. An aliquot was used for the determination of protein concentration using BCA™ protein assay kit (PIERCE) and the measurement was made on Wallac 1420 ARVOsx multilabel counter with BSA as a standard.

For the binding experiments, 20 μL of test compounds were incubated with 20 μL of [$^3$H] CP55,940 (Perkin Elmer, final 1 nM) and 160 μL of membrane homogenate (1 μg protein/tube) for 60 minutes at 37° C. Nonspecific binding was determined by 1 μM CP55,940 (TOCRIS Cookson Inc) at the final concentration. All incubations were harvested by vacuum filtration through GF/B fiber filters pre-soaked in 5% BSA in TME buffer using Uni-Filter cell harvester (Packard). Filters were rinsed with wash buffer (25 mM Tris-HCl (pH7.4), 5 mM $MgCl_2$, 1 mM EDTA) and then dried up at 50° C. for 30 min. The radioactivity was measured by scintillation counting using Top-Count Microplate Scintillation Counter (Packard). Rat CB1 binding affinities were also determined by a method similar to the above by using rat whole brains.

All compounds of Examples showed selective CB2 receptor affinity.

Human CB2 Binding

Human CB2 transfected Chinese hamster ovary K1 (CHO-K1) cells were established and grown to 60-80% confluence. The collected cell pastes were washed with cold PBS, suspended in 50 mM Tris-HCl (pH7.4 at 25° C.) containing protease inhibitor cocktail and homogenized using a hand held Polytron PT 1200 disruptor set at 25,000 rpm for 30 seconds on ice. The homogenates were centrifuged at 1,000×g at 4° C. for 10 min. The supernatant was recovered and centrifuged at 40,000×g at 4° C. for 10 min. The pellets were then resuspended in 50 mM Tris-HCl (pH7.4 at 25° C.). This suspension was centrifuged once more in the same manner. The final pellet was resuspended in TME buffer (25 mM Tris-HCl (pH7.4), 5 mM $MgCl_2$, 1 mM EDTA, 0.5% BSA), aliquoted and stored at −80° C. until assayed. An aliquot was used for the determination of protein concentration using BCA™ protein assay kit (PIERCE) and the measurement was made on Wallac 1420 ARVOsx multilabel counter with BSA as a standard.

For the binding experiments, 20 μL of test compounds were incubated with 20 μL of [$^3$H] CP55,940 (Perkin Elmer, final 1 nM) and 160 μL of membrane homogenate (1 μg protein/tube) for 60 minutes at 37° C. Nonspecific binding was determined by 1 μM CP55,940 (TOCRIS Cookson Inc) at the final concentration.

All incubations were harvested by vacuum filtration through GF/B fiber filters pre-soaked in 5% BSA in TME buffer using Uni-Filter cell harvester (Packard). Filters were rinsed with wash buffer (25 mM Tris-HCl (pH7.4), 5 mM MgCl$_2$, 1 mM EDTA) and then dried up at 50° C. for 30 min. The radioactivity was measured by scintillation counting using Top-Count Microplate Scintillation Counter (Packard). Human CB1 binding affinities were also determined by a method similar to the above by using Human CB1 transfected Chinese hamster ovary-K1 (CHO-K1) cells, [$^3$H] SR141716A (Amersham Bioscience) and AM251 (TOCRIS Cookson Inc).

All compounds of Examples showed selective CB2 receptor affinity.

Agonist-induced cAMP Change in Human CB2 Transfected CHO-K1 Cells

Human CB2 transfected Chinese hamster ovary-K1 (CHO-K1) cells were established and grown to 60-80% confluence. The medium was changed to F-12 medium containing 10% dialysed FBS, and the cells were incubated overnight. On the day of the assay, the cells were harvested with PBS/1 mM EDTA, centrifuged and washed with PBS. Cell pellets were resuspended in the incubation buffer (F-12 medium, 20 mM HEPES, 1 mM IBMX, 0.1 mM Ro-20-1724) at the concentration of 1×10$^5$ cells/ml and pre-incubated for 15 min at room temperature. The agonist samples were diluted from 10 mM stock solution in DMSO and dispensed into 96-well half-area plates (12.5 µl/well) with assay buffer (F-12, 20 mM HEPES). The reaction was initiated by adding the cells (25 µl/well) into the well containing forskolin (12.5 µL/well, final 5 µM) and diluted compounds. After incubation for 30 minutes at 37° C., cAMP-XL665 conjugated, and then the anti-cAMP-cryptase conjugate was added to the lysate (25 µl/well each). After further incubation for 60 minutes at room temperature, measurements were made on the Wallac 1420 ARVOsx multilabel counter (Excitation 320 nm, Emission 665 nm/620 nm, delay time 50 µs, window time 400 µs). Data analysis was made based on the ratio of fluorescence intensity of each well at 620 nm and 665 nm. The equation "sigmoldal dose-response" was used for the determination of EC$_{50}$ and Emax values.

Results are shown in Table 1. All compounds of Examples showed CB2 receptor agonistic activity as shown in the following table.

TABLE 1

| Example # | EC$_{50}$(nM) | Emax(%) |
|---|---|---|
| 1 | 0.91 | 118 |
| 2 | 0.15 | 160 |
| 3 | 0.45 | 121 |
| 4 | 1.31 | 114 |
| 5 | 5.53 | 118 |
| 6 | 2.96 | 136 |
| 7 | 1.34 | 141 |
| 8 | 6.68 | 129 |
| 9 | 1.13 | 127 |
| 10 | 3.64 | 109 |
| 11 | 13.7 | 117 |
| 12 | 5.34 | 133 |
| 13 | 5.24 | 113 |
| 14 | 1.59 | 120 |
| 15 | 8.31 | 113 |
| 16 | 1.22 | 109 |
| 17 | 1.98 | 120 |
| 18 | 26.4 | 109 |
| 19 | 3.77 | 110 |

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM MgCl$_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 µL in 96-well plates. Twenty µL of test compounds were incubated with 20 µL of [$^3$H]-dofetilide (Amersham, final 5 nM) and 160 µL of membrane homogenate (25 µg protein) for 60 minutes at room temperature. Nonspecific binding was determined by 10 µM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM MgCl$_2$, pH 7.4 at 4° C. The filters were dried, put into sample bags and filled with Betaplate Scint. Radioactivity bound to filter was counted with Wallac Betaplate counter.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.5 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM CaCl$_2$ and 0.5 mM MgCl$_2$ (pH 6.5). The basolateral buffer consisted of Hanks Balanced Salt Solution, 25 mM D-glucose monohydrate, 20 mM HEPES Biological Buffer, 1.25 mM CaCl$_2$ and 0.5 mM MgCl$_2$ (pH 7.4). At the end of the preincubation, the media was removed and test compound solution (10 µM) in buffer was added to the apical compartment. The inserts were moved to wells containing fresh basolateral buffer at 1 hr. Drug concentration in the buffer was measured by LC/MS analysis.

Flux rate (F, mass/time) was calculated from the slope of cumulative appearance of substrate on the receiver side and apparent permeability coefficient (P$_{app}$) was calculated from the following equation.

$$P_{app} \text{(cm/sec)} = (F*VD)/(SA*MD)$$

where SA is surface area for transport (0.3 cm$^2$), VD is the donor volume (0.3 ml), MD is the total amount of drug on the donor side at t=0. All data represent the mean of 2 inserts. Monolayer integrity was determined by Lucifer Yellow transport.

Half-life in Human Liver Microsomes (HLM)

Test compounds (1 µM) were incubated with 3.3 mM MgCl$_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=ln 2/k

TNBS-induced Chronic Colonic Allodynia in the Rat

Male, IGS (Sprague-Dawley) rats, 240-270 g (7 weeks, Charles River Japan) are used. Environment conditions are controlled at a 12-h light/dark cycle with lights on at 07:00 and an ambient temperature of 23+/−2° C. Rats are housed under this condition for 4 days before the surgery. Each group is used a group of 6-8 rats. Rats are fasted for 24 hours before use. After weighing and administration of the anesthetic (Ketamine/Xylazine), the animal is placed in the dorsal decubitus position. The abdomen is shaved and disinfected with 10% povidoneiodine solution (isodine). A 2-cm long median laparotomy is conducted by making the incision 3 cm from the sternum. The cecum is then found, grasped with the fingers, removed from the abdominal cavity and placed on a compress that has been previously moistened with isotonic saline. TNBS (Fluka; 50 mg/kg; 1.5 ml/kg in 30% EtOH) is injected into the proximal colon (1 cm from the cecum). Sham group's animal undergoes the same surgery but TNBS is not injected. After injection, the intestines are put back into the abdominal cavity. The muscle wall is then sutured with silk, using two cross-stitches. The skin is also sutured. After 7 days from the surgery, the balloon (5 cm in length) is inserted through the anus and kept in position (tip of balloon is 5 cm from the anus) by taping the catheter to the base of the tail. The animals are individually placed without restraint in cages for distention session. The balloon is progressively inflated by step of 5 mm Hg, from 0 to 70 mm Hg, each step of inflation lasting 30 s. Each cycle of colonic distention is controlled by a standard barostat (G&J Electronic Inc. CANADA). The pain threshold corresponds to the pressure that produced the first abdominal contraction. The abdominal contraction corresponds to waves of contraction of oblique musculature with inward turning of the hindlimb, or to humpbacked position, or to squashing of the lower abdomen against the floor (Wesselmann U et al., (1998) Neurosci Lett 246: 73-76). To determine the basal colonic threshold, two cycles of distention are performed on the same animal with an interval of >10 min before compound administration. The 1st distention is conducted to acclimate the rat to the colonic distention. The baseline is determined by the second distention. The effect of a test compound on the colonic threshold is investigated at X min post dosing. If necessary, the time course of effect of a test compound may be studied at different times.

Distribution of the treatment groups is as follows:

|                    | Injection of TNBS | Treatment     |
|--------------------|-------------------|---------------|
| Sham control group | No                | Vehicle       |
| TNBS control group | Yes               | Vehicle       |
| Treated group      | Yes               | Test compound |

The data are expressed as median threshold (mmHg) required to induce abdominal contractions in each group (vertical bars represent 1st and 3rd quartiles). Data are analyzed using Kruskal-Wallis test followed by Mann-Whitney U-test.

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230-400 mesh ASTM) or Fuji Silysia Chromatorex® DU3050 (Amino Type, 30~50 μm). Low-resolution mass spectral data (EI) were obtained on a integrity (Waters) mass spectrometer or a Automass 120 (JEOL) mass spectrometer. Low-resolution mass spectral data (ESI) were obtained on a ZMD2 (Waters) mass spectrometer or a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. IR spectra were measured by a Shimazu infrared spectrometer (IR-470). Optical rotations were measured using a JASCO DIP-370 Digital Polarimeter (Japan Spectroscopic Co., Ltd.). Chemical symbols have their usual meanings; b.p. (boiling point), m.p. (melting point), L (liter(s)), mL (milliliter(s)), g (gram(s)), mg (milligram(s)), mol (moles), mmol (millimoles), eq. (equivalent(s)).

Example 1

2-{[1-(Cyclopropylmethyl)-2-(2,2-dimethylpropyl)-1H-benzimidazol-5-yl]sulfonyl}-2-methylpropanamide

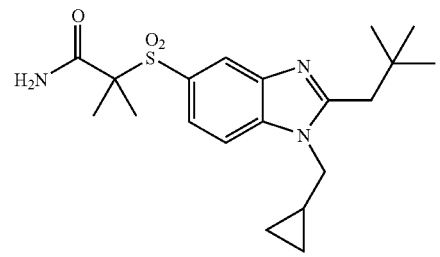

Step A. 4-Bromo-N-(cyclopropylmethyl)-2-nitroaniline

A mixture of 4-bromo-1-fluoro-2-nitrobenzene (10.3 g, 46.9 mmol), cyclopropanemethylamine (5.0 g, 70.3 mmol) and N,N'-diisopropylethylamine (15.1 g, 117 mmol) in ethanol (116 mL) was stirred at reflux temperature for 15 h. After cooling to room temperature, the mixture was concentrated under reduced pressure. The residue was purified by column chromatography on silica gel (ethyl acetate as eluent) to afford the title compound (12.7 g, quant.) as an orange solid.

$^1$H-NMR (CDCl$_3$) δ: 8.32 (d, J=2.4 Hz, 1H), 8.11 (br, 1H), 7.49-7.46 (m, 1H), 6.72 (d, J=9.2 Hz, 1H), 3.16-3.11 (m, 2H), 1.20-1.14 (m, 1H), 0.69-0.62 (m, 2H), 0.35-0.29 (m, 2H). MS (ESI) 271 (M+H)$^+$.

Step B. 4-Bromo-N$^1$-(cyclopropylmethyl)benzene-1,2-diamine

A mixture of 4-bromo-N-(cyclopropylmethyl)-2-nitroaniline (Step A, 12.7 g, 47.0 mmol), iron (13.1 g, 470 mmol) and ammonium chloride (250 mg, 4.70 mmol) in ethanol (126 mL) and water (42 mL) was stirred at reflux temperature for 3 h. After cooling to room temperature, the mixture was filtered and the filtrate was concentrated under reduced pressure. The residue was dissolved in ethyl acetate (100 mL) and water (50 mL). The organic layer was separated, washed with brine (20 mL), dried over magnesium sulfate and concentrated to afford the title compound (11.3 g, 99%) as a brown oil.

$^1$H-NMR (CDCl$_3$) δ: 6.88 (dd, J=8.4, 2.2 Hz, 1H), 6.83 (d, J=2.2 Hz, 1H), 6.47 (d, J=8.4 Hz, 1H), 3.41 (br, 3H), 2.90 (d, J=6.8 Hz, 1H), 1.19-1.06 (m, 1H), 0.60-0.54 (m, 2H), 0.27-0.22 (m, 2H). MS (ESI) 241 (M+H)$^+$.

Step C. N-{5-Bromo-2-[(cyclopropylmethyl)amino]phenyl}-3,3-dimethylbutanamide

To a solution of 4-bromo-N$^1$-(cyclopropylmethyl)benzene-1,2-diamine (Step B, 11.3 g, 46.9 mmol) and N,N'-diisopropylethylamine (6.06 g, 46.9 mmol) in ethyl acetate (88 mL) was added tert-butylacetyl chloride (6.31 g, 46.9 mmol) at 0° C. and the mixture was allowed to warm to room temperature for 15 h. The mixture was washed with saturated sodium hydrogencarbonate aqueous solution-(100 mL×2), brine (50 mL), dried over magnesium sulfate and concentrated under reduced pressure. The residue was washed with ethyl acetate to afford the title compound (11.2 g, 70%) as a white solid.

$^1$H-NMR (CDCl$_3$) δ: 7.42 (d, J=2.0 Hz, 1H), 7.21 (dd, J=8.6, 2.0 Hz, 1H), 6.97 (br, 1H), 6.59 (d, J=8.6 Hz, 1H), 3.95 (br, 1H), 2.89 (d, J=7.1 Hz, 2H), 2.28 (s, 2H), 1.14-0.98 (m, 10H), 0.61-0.52 (m, 2H), 0.27-0.21 (m, 2H). MS (ESI) 339 (M+H)$^+$, 337 (M−H)$^−$.

Step D. 5-Bromo-1-(cyclopropylmethyl)-2-(2,2-dimethylpropyl)-1H-benzimidazole

A mixture of N-{5-bromo-2-[(cyclopropylmethyl)amino]phenyl}-3,3-dimethylbutanamide (Step C, 11.2 g, 33.0 mmol) and p-toluenesulfonic acid monohydrate (6.29 g, 33.0 mmol) in toluene (240 mL) was stirred at reflux temperature for 20 h with Dean-Stark apparatus. The mixture was cooled to 0° C. and a precipitate formed. The precipitate was collected by filtration washing with ethyl acetate. The precipitate was dissolved in ethyl acetate (200 mL) and saturated sodium hydrogencarbonate aqueous solution (100 mL). The organic layer was separated, washed with brine (20 mL), dried over magnesium sulfate and concentrated under reduced pressure. The residue was purified by column chromatography on silica gel (hexane:ethyl acetate=3:1 as eluent) to give the title compound (10.1 g, 95%) as a white solid.

$^1$H-NMR (CDCl$_3$) δ: 7.88 (d, J=1.8 Hz, 1H), 7.33 (dd, J=8.5, 1.8 Hz, 1H), 7.22 (d, J=8.5 Hz, 1H), 4.05 (d, J=7.2 Hz, 2H), 2.80 (s, 2H), 1.19-1.10 (m, 1H), 1.07 (s, 9H), 0.63-0.57 (m, 2H), 0.38-0.33 (m, 2H). MS (ESI) 321 (M+H)$^+$.

Step E. Methyl {[1-(cyclopropylmethyl)-2-(2,2-dimethylpropyl)-1H-benzimidazol-5-yl]thio}acetate To a solution of 5-bromo-1-(cyclopropylmethyl)-2-(2,2-dimethylpropyl)-1H-benzimidazole (Step D, 4.0 g, 12.5 mmol) in 1,4-dioxane (25 mL) were added N,N'-diisopropylethylamine (4.4 mL, 25 mmol), methyl mercaptoacetate (1.1 ml, 12.5 mmol), tris(dibenzylideneacetone)dipalladium(0) (284 mg, 0.31 mmol) and 4,5-bis(diphenylphosphino)-9,9-dimethylxanthene (362 mg, 0.63 mmol). The mixture was stirred at reflux temperature for 24 h under nitrogen atmosphere. After cooling to room temperature, the mixture was filtered and the filtrate was concentrated under reduced pressure. The residue was purified by column chromatography on silica gel (hexane:ethyl acetate=2:1 as eluent) to afford the title compound (4.75 g, quant.) as a pale yellow oil.

$^1$H-NMR (CDCl$_3$) δ: 7.88 (d, J=1.5 Hz, 1H), 7.37 (dd, J=8.1, 1.5 Hz, 1H), 7.30 (d, J=8.1 Hz, 1H), 4.05 (d, J=6.6 Hz, 2H), 3.71 (s, 3H), 3.64 (s, 2H), 2.81 (s, 2H), 1.22-1.13 (m, 1H), 1.08 (s, 9H), 0.63-0.57 (m, 2H), 0.39-0.34 (m, 2H). MS (ESI) 347 (M+H)$^+$.

Step F. Methyl {[1-(cyclopropylmethyl)-2-(2,2-dimethylpropyl)-1H-benzimidazol-5-yl]sulfonyl}acetate To a solution of methyl {[1-(cyclopropylmethyl)-2-(2,2-dimethylpropyl)-1H-benzimidazol-5-yl]thio}acetate (Step E, 4.75 g, 12.5 mmol) in dichloromethane (100 mL) was added m-chloroperbenzoic acid (6.75 g, 27.4 mmol) portionwise at 0° C. The mixture was allowed to warm to room temperature for 3 h. The mixture was quenched with sodium sulfite aqueous solution and extracted with dichloromethane (50 mL). The organic layer was washed with saturated sodium hydrogencarbonate aqueous solution, dried over sodium sulfate and concentrated under reduced pressure. The residue was purified by column chromatography on silica gel (hexane:ethyl acetate=2:1 to 1:1 as eluent) to afford the title compound (4.33 g, 91%) as a yellow solid.

$^1$H-NMR (CDCl$_3$) δ: 8.35 (br s, 1H), 7.83 (dd, J=8.8, 1.5 Hz, 1H), 7.50 (d, J=8.8 Hz, 1H), 4.17 (s, 2H), 4.12 (d, J=6.6 Hz, 2H), 3.73 (s, 3H), 2.86 (s, 2H), 1.15-1.06 (m, 10H), 0.70-0.60 (m, 2H), 0.44-0.35 (m, 2H). MS (ESI) 379 (M+H)$^+$.

Step G. Methyl 2-{[1-(cyclopropylmethyl)-2-(2,2-dimethylpropyl)-1H-benzimidazol-5-yl]sulfonyl}-2-methylpropanoate To a solution of methyl {[1-(cyclopropylmethyl)-2-(2,2-dimethylpropyl)-1H-benzimidazol-5-yl]sulfonyl}acetate (Step F, 1.0 g, 2.64 mmol) in N,N'-dimethylformamide (11.5 mL) was added sodium hydride (233 mg, 5.81 mmol) and methyl iodide (825 mg, 5.81 mmol) at 0° C. The mixture was stirred at room temperature for 15 h. The mixture was quenched with water (120 mL) and extracted with ethyl acetate (60 mL×4). The combined organic layers were washed with water (50 mL×4), brine (20 mL), dried over magnesium sulfate and concentrated under reduced pressure. The residue was purified by column chromatography on silica gel (hexane:ethyl acetate=1:1 as eluent) to afford the title compound (1.12 g, quant.) as a yellow oil.

$^1$H-NMR (CDCl$_3$) δ: 8.26 (br s, 1H), 7.71, (dd, J=8.1, 2.2 Hz, 1H), 7.46 (d, J=8.1 Hz, 1H), 4.12 (d, J=6.6 Hz, 2H), 3.71 (s, 3H), 2.85 (s, 2H), 1.65 (s, 6H), 1.20-1.03 (m, 10H), 0.71-0.57 (m, 2H), 0.46-0.32 (m, 2H). MS (ESI) 407 (M+H)$^+$.

Step H. 2-{[1-(Cyclopropylmethyl)-2-(2,2-dimethylpropyl)-1H-benzimidazol-5-yl]sulfonyl}-2-methylpropanoic Acid To a solution of methyl 2-{[1-(cyclopropylmethyl)-2-(2,2-dimethylpropyl)-1H-benzimidazol-5-yl]sulfonyl}-2-methylpropanoate (Step G, 1.07 g, 2.64 mmol) in methanol (5 mL) and tetrahydrofuran (5 mL) was added 2N sodium hydroxide aqueous solution (5 mL) at room temperature. The mixture was stirred at room temperature for 3 h. The mixture was made acidic with 2N hydrochloric acid (pH ~4) and concentrated under reduced pressure. The residue was dissolved in water (50 mL) and dichloromethane (50 mL). The aqueous layer was separated and extracted with dichloromethane (50 mL×2). The combined organic layers were dried over magnesium sulfate and concentrated under reduced pressure to afford the title compound (920 mg, 89%) as a white solid.

$^1$H-NMR (CDCl$_3$) δ: 8.56 (d, J=1.5 Hz, 1H), 7.86 (dd, J=8.8, 1.5 Hz, 1H), 7.52 (d J=8.8 Hz, 1H), 4.10 (d, J=6.6 Hz, 2H), 2.89 (s, 2H), 1.72 (s, 6H), 1.22-1.11 (m, 1H), 0.98 (s, 9H), 0.66-0.60 (m, 2H), 0.41-0.36 (m, 2H), a peak of COOH was not observed. MS (ESI) 393 (M+H)$^+$, 391 (M−H)$^−$.

Step I. 2-{[1-(Cyclopropylmethyl)-2-(2,2-dimethylpropyl)-1H-benzimidazol-5-yl]sulfonyl}-2-methylpropanamide To a suspension of 2-{[1-(cyclopropylmethyl)-2-(2,2-dimethylpropyl)-1H-benzimidazol-5-yl]sulfonyl}-2-methylpropanoic acid (Step H, 200 mg, 0.51 mmol) and di-tert-butyl dicarbonate (145 mg, 0.66 mmol) in acetonitrile (3 mL) were added ammonium bicarbonate (48 mg, 0.61 mmol) and pyridine (48 mg, 0.61 mmol) at room temperature. The mixture was stirred at room temperature for 20 h and concentrated under reduced pressure. The residue was dissolved in water (30 mL) and dichloromethane (30 mL). The aqueous layer was separated and extracted with dichloromethane (30 mL). The combined organic layers were dried over magnesium sulfate and concentrated under reduced pressure. The residue was purified by column chromatography on silica gel (hexane:ethyl acetate=1:3 as eluent) to afford the title compound (200 g, quant.) as a white solid.

$^1$H-NMR (CDCl$_3$) δ: 8.31 (d, J=2.0 Hz, 1H), 7.75 (dd, J=8.6, 2.0 Hz, 1H), 7.47 (d J=8.6 Hz, 1H), 7.20 (br, 1H), 5.59 (br, 1H), 4.11 (d, J=6.6 Hz, 2H), 2.85 (s, 2H), 1.62 (s, 6H), 1.28-1.12 (m, 1H), 1.11 (s, 9H), 0.69-0.62 (m, 2H), 0.43-0.37 (m, 2H). MS (ESI) 392 (M+H)$^+$, 390 (M−H)$^−$.

Example 2

1-{[1-(Cyclopropylmethyl)-2-(2,2-dimethylpropyl)-1H-benzimidazol-5-yl]sulfonyl}cyclopropanecarboxamide

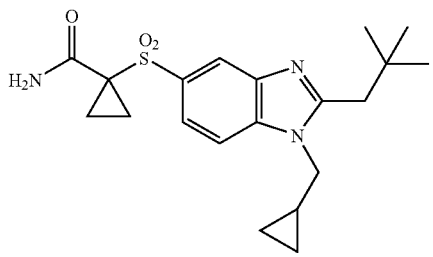

Step A. Methyl 1-{[1-(cyclopropylmethyl)-2-(2,2-dimethylpropyl)-1H-benzimidazol-5-yl]sulfonyl}cyclopropanecarboxylate To a solution of methyl {[1-(cyclopropylmethyl)-2-(2,2-dimethylpropyl)-1H-benzimidazol-5-yl]sulfonyl}acetate (Example 1, Step F, 620 mg, 1.64 mmol) in N,N'-dimethylformamide (6.0 mL) was added potassium carbonate (680 mg, 4.91 mmol) and 1,2-dibromoethane (170 μL, 1.97 mmol) at room temperature and stirred for 30 h. The mixture was quenched with water (40 mL) and extracted with ethyl acetate (50 mL×3). The combined organic layers were dried over sodium sulfate and concentrated under reduced pressure. The residue was purified by column chromatography on silica gel (hexane:ethyl acetate=3:2 as eluent) to afford the title compound (533 mg, 80%) as a white amorphous.

$^1$H-NMR (CDCl$_3$) δ: 8.33 (d, J=1.5 Hz, 1H), 7.96 (dd, J=8.1, 1.5 Hz, 1H), 7.47 (d, J=8.8 Hz, 1H), 4.12 (d, J=6.6 Hz, 2H), 3.63 (s, 3H), 2.85 (s, 2H), 2.08-2.01 (m, 2H), 1.73-1.66 (m, 2H), 1.25-1.17 (m, 1H), 1.10 (s, 9H), 0.69-0.60 (m, 2H), 0.44-0.36 (m, 2H). MS (ESI) 405 (M+H)$^+$.

Step B. 1-{[1-(Cyclopropylmethyl)-2-(2,2-dimethylpropyl)-1H-benzimidazol-5-yl]sulfonyl}cyclopropanecarboxylic Acid The title compound was prepared according to the procedure described in Step H of Example 1 using methyl 1-{[1-(cyclopropylmethyl)-2-(2,2-dimethylpropyl)-1H-benzimidazol-5-yl]sulfonyl}cyclopropanecarboxylate (Step A) instead of methyl 2-{[1-(cyclopropylmethyl)-2-(2,2-dimethylpropyl)-1H-benzimidazol-5-yl]sulfonyl}-2-methylpropanoate.

$^1$H-NMR (CDCl$_3$) δ: 8.17 (d, J=1.5 Hz, 1H), 7.77 (dd, J=8.8, 1.5 Hz, 1H), 7.70 (d J=8.8 Hz, 1H), 4.21 (d, J=6.6 Hz, 2H), 2.83 (s, 2H), 1.55-1.47 (m, 2H), 1.35-1.28 (m, 2H), 1.07 (s, 9H), 1.10-1.02 (m, 1H), 0.53-0.39 (m, 4H), a peak of COOH was not observed. MS (ESI) 391 (M+H)$^+$, 389 (M−H)$^−$.

Step C. 1-{[1-(Cyclopropylmethyl)-2-(2,2-dimethylpropyl)-1H-benzimidazol-5-yl]sulfonyl}cyclopropanecarboxamide The title compound was prepared according to the procedure described in Step I of Example 1 using 1-{[1-(cyclopropylmethyl)-2-(2,2-dimethylpropyl)-1H-benzimidazol-5-yl]sulfonyl}cyclopropanecarboxylic acid (Step B) instead of 2-{[1-(cyclopropylmethyl)-2-(2,2-dimethylpropyl)-1H-benzimidazol-5-yl]sulfonyl}-2-methylpropanoic acid.

$^1$H-NMR (CDCl$_3$) δ: 8.32 (d, J=2.2 Hz, 1H), 7.89 (br s, 1H), 7.75 (dd, J=8.8, 2.2 Hz, 1H), 7.47 (d J=8.8 Hz, 1H), 5.60 (br s, 1H), 4.12 (d, J=6.6 Hz, 2H), 2.85 (s, 2H), 1.89-1.82 (m, 2H), 1.71-1.65 (m, 2H), 1.22-1.13 (m, 1H), 1.10 (s, 9H), 0.70-0.61 (m, 2H), 0.44-0.35 (m, 2H). MS (ESI) 390 (M+H)$^+$.

Example 3

1-{[1-(Cyclopropylmethyl)-2-(2,2-dimethylpropyl)-1H-benzimidazol-5-yl]sulfonyl}cyclobutanecarboxamide

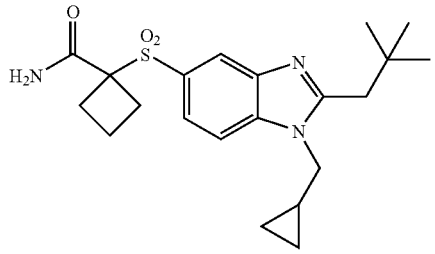

Step A. Methyl 1-{[1-(cyclopropylmethyl)-2-(2,2-dimethylpropyl)-1H-benzimidazol-5-yl]sulfonyl}cyclobutanecarboxylate The title compound was prepared according to the procedure described in Step G of Example 1 using 1,3-dibromopropane instead of methyl iodide.

¹H-NMR (CDCl₃) δ: 8.24 (d, J=1.3 Hz, 1H), 7.67 (dd, J=8.6, 1.3 Hz, 1H), 7.45 (d, J=8.6 Hz, 1H), 4.10 (d, J=6.6 Hz, 2H), 3.68 (s, 3H), 3.06-2.95 (m, 2H), 2.84 (s, 2H), 2.65-2.56 (m, 2H), 2.21-2.07 (m, 1H), 2.01-1.89 (m, 1H), 1.26-1.14 (m, 1H), 1.09 (s, 9H), 0.67-0.60 (m, 2H), 0.42-0.36 (m, 2H). MS (ESI) 419 (M+H)⁺.

Step B. 1-{[1-(Cyclopropylmethyl)-2-(2,2-dimethylpropyl)-1H-benzimidazol-5-yl]sulfonyl}cyclobutanecarboxylic Acid The title compound was prepared according to the procedure described in Step H of Example 1 using methyl 1-{[1-(cyclopropylmethyl)-2-(2,2-dimethylpropyl)-1H-benzimidazol-5-yl]sulfonyl}cyclobutanecarboxylate (Step A) instead of methyl 2-{[1-(cyclopropylmethyl)-2-(2,2-dimethylpropyl)-1H-benzimidazol-5-yl]sulfonyl}-2-methylpropanoate.

¹H-NMR (CDCl₃) δ: 8.52 (d, J=1.7 Hz, 1H), 7.81 (dd, J=8.6, 1.7 Hz, 1H), 7.49 (d J=8.6 Hz, 1H), 4.08 (d, J=6.6 Hz, 2H), 3.15-3.02 (m, 2H), 2.94 (s, 2H), 2.73-2.63 (m, 2H), 2.26-1.99 (m, 2H), 1.21-1.09 (m, 1H), 0.98 (s, 9H), 0.67-0.59 (m, 2H), 0.42-0.36 (m, 2H), a peak of COOH was not observed. MS (ESI) 405 (M+H)⁺, 403 (M−H)⁻.

Step C. 1-{[1-(Cyclopropylmethyl)-2-(2,2-dimethylpropyl)-1H-benzimidazol-5-yl]sulfonyl}cyclobutanecarboxamide The title compound was prepared according to the procedure described in Step I of Example 1 using 1-{[1-(cyclopropylmethyl)-2-(2,2-dimethylpropyl)-1H-benzimidazol-5-yl]sulfonyl}cyclobutanecarboxylic acid (Step B) instead of 2-{[1-(cyclopropylmethyl)-2-(2,2-dimethylpropyl)-1H-benzimidazol-5-yl]sulfonyl}-2-methylpropanoic acid.

¹H-NMR (CDCl₃) δ: 8.28 (d, J=1.7 Hz, 1H), 7.70 (dd, J=8.6, 1.7 Hz, 1H), 7.44 (d J=8.6 Hz, 1H), 6.89 (br, 1H), 5.50 (br, 1H), 4.09 (d, J=6.6 Hz, 2H), 3.02-2.91 (m, 2H), 2.84 (s, 2H), 2.70-2.59 (m, 2H), 2.18-1.96 (m, 2H), 1.26-1.14 (m, 1H), 1.10 (s, 9H), 0.68-0.61 (m, 2H), 0.42-0.36 (m, 2H). MS (ESI) 404 (M+H)⁺.

Example 4

4-{[1-(Cyclopropylmethyl)-2-(2,2-dimethylpropyl)-1H-benzimidazol-5-yl]sulfonyl}tetrahydro-2H-pyran-4-carboxamide

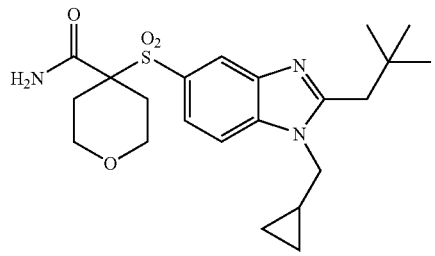

Step A. Methyl 4-{[1-(cyclopropylmethyl)-2-(2,2-dimethylpropyl)-1H-benzimidazol-5-yl]sulfonyl}tetrahydro-2H-pyran-4-carboxylate The title compound was prepared according to the procedure described in Step G of Example 1 using 2-bromomethyl ether (Aldrich Chemical Company, Inc.) instead of methyl iodide.

¹H-NMR (CDCl₃) δ: 8.21 (d, J=1.3 Hz, 1H), 7.65 (dd, J=8.6, 1.3 Hz, 1H), 7.47 (d, a 8.6 Hz, 1H), 4.12 (d, J=5.9 Hz, 2H), 4.02-3.96 (m, 2H), 3.77 (s, 3H), 3.31-3.22 (m, 2H), 2.85 (s, 2H), 2.35-2.18 (m, 4H), 1.26-1.15 (m, 1H), 1.11 (s, 9H), 0.69-0.62 (m, 2H), 0.43-0.37 (m, 2H). MS (ESI) 449 (M+H)⁺.

Step B. 4-{[1-(Cyclopropylmethyl)-2-(2,2-dimethylpropyl)-1H-benzimidazol-5-yl]sulfonyl}tetrahydro-2H-pyran-4-carboxylic Acid The title compound was prepared according to the procedure described in Step H of Example 1 using methyl 4-{[1-(cyclopropylmethyl)-2-(2,2-dimethylpropyl)-1H-benzimidazol-5-yl]sulfonyl}tetrahydro-2H-pyran-4-carboxylate (Step A) instead of methyl 2-{[1-(cyclopropylmethyl)-2-(2,2-dimethylpropyl)-1H-benzimidazol-5-yl]sulfonyl}-2-methylpropanoate.

¹H-NMR (CDCl₃) δ: 7.94 (d, J=1.5 Hz, 1H), 7.85 (d, J=8.8 Hz, 1H), 7.58 (dd J=8.8, 1.5 Hz, 1H), 4.24 (d, J=7.3 Hz, 2H), 3.94-3.90 (m, 2H), 3.18-3.11 (m, 2H), 2.86 (s, 2H), 2.11-1.94 (m, 4H), 1.28-1.13 (m, 1H), 1.08 (s, 9H), 0.53-0.41 (m, 4H), a peak of COOH was not observed. MS (ESI) 435 (M+H)⁺.

Step C. 4-{[1-(Cyclopropylmethyl)-2-(2,2-dimethylpropyl)-1H-benzimidazol-5-yl]sulfonyl}tetrahydro-2H-pyran-4-carboxamide A mixture of 4-{[1-(cyclopropylmethyl)-2-(2,2-dimethylpropyl)-1H-benzimidazol-5-yl]sulfonyl}tetrahydro-2H-pyran-4-carboxylic acid (Step B, 288 mg, 0.66 mmol), thionyl chloride and N,N-dimethylformamide (few drops) was stirred under reflux for 3 h. After concentration, the residue was dissolved in dichloromethane (10 mL) and aqueous ammonia (1 mL) was added. The mixture was stirred at room temperature for 4 days. Water was added and the organic layer was separated. The organic layer was dried over sodium sulfate and concentrated under reduced pressure. The residue was purified by pTLC (hexane:ethyl acetate=1:10 as eluent) to give the title compound (264 mg, 92%) as a white solid.

¹H-NMR (CDCl₃) δ: 8.26 (d, J=2.0 Hz, 1H), 7.71 (dd, J=8.6, 2.0 Hz, 1H), 7.47 (d J=8.6 Hz, 1H), 6.89 (br, 1H), 5.69 (br, 1H), 4.10 (d, J=6.6 Hz, 2H), 3.99-3.94 (m, 2H), 3.56-3.46 (m, 2H), 2.85 (s, 2H), 2.35-2.12 (m, 4H), 1.26-1.16 (m, 1H), 1.11 (s, 9H), 0.70-0.63 (m, 2H), 0.43-0.37 (m, 2H). MS (ESI) 434 (M+H)⁺.

Example 5

2-{[3-(Cyclopropylmethyl)-2-(2,2-dimethylpropyl)-3H-imidazo[4,5-b]pyridin-6-yl]sulfonyl}-2-methylpropanamide

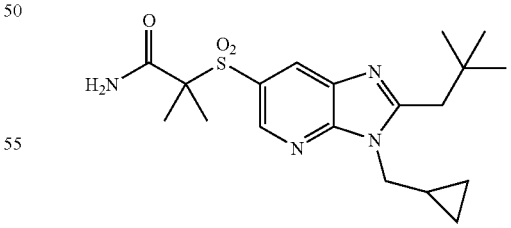

Step A. 5-Bromo-3-nitropyridin-2(1H)-one

To a solution of 5-bromopyridin-2(1H)-one (Aldrich, 10 g, 57.5 mmol) in sulfuric acid (60 mL) was added nitric acid (60-61%, Wako Pure Chemical Industries, Ltd., 20 mL) at 0° C. The mixture was allowed to warm to room temperature and stirred for 4.5 h. The mixture was poured into ice water and obtained precipitate was collected by filtration. The solid was washed with water and dried in vacuo to afford the title compound (7.2 g, 57%) as a yellow solid.

$^1$H-NMR (CDCl$_3$) δ: 13.21 (br, 1H), 8.55 (d, J=2.6 Hz, 1H), 8.19 (d, J=2.6 Hz, 1H). MS (ESI) 217 (M−H)$^−$.

Step B. 5-Bromo-2-chloro-3-nitropyridine

A mixture of 5-bromo-3-nitropyridin-2(1H)-one (Step A, 7.2 g, 32.9 mmol), phosphoryl chloride (72 mL) and N,N-dimethylformamide (7.2 mL) was stirred under reflux for 2 h. After removal of solvent, the residue was dissolved in water (100 mL) and ethyl acetate (30 mL) and the solution was separated. The organic layer was washed with saturated sodium hydrogen carbonate, dried over sodium sulfate and concentrated to afford the title compound (6.97 g, 89%) as a pale yellow solid.

$^1$H-NMR (CDCl$_3$) δ: 8.70 (d, J=1.7 Hz, 1H), 8.37 (d, J=1.7 Hz, 1H).

Step C. 5-Bromo-N-(cyclopropylmethyl)-3-nitropyridin-2-amine

A mixture of 5-bromo-2-chloro-3-nitropyridine (Step B, 5.0 g, 21.1 mmol), cyclopropanemethylamine (2.8 mL, 31.7 mmol) and N,N-diisopropylethylamine (5.5 mL, 31.7 mmol) in ethanol (20 mL) was stirred at room temperature for 24 h. After cooling to room temperature, the mixture was concentrated under reduced pressure. The residue was purified by column chromatography on silica gel (ethyl acetate as eluent) to afford the title compound (5.5 g, 96%) as a yellow solid.

$^1$H-NMR (CDCl$_3$) δ: 8.55 (d, J=2.3 Hz, 1H), 8.43 (d, J=2.3 Hz, 1H), 3.47 (dd, J=6.6, 5.3 Hz, 2H), 1.20-1.11 (m, 1H), 0.64-0.57 (m, 2H), 0.35-0.29 (m, 2H). MS (ESI) 272 (M+H)$^+$.

Step D. 5-Bromo-N$^2$-(cyclopropylmethyl)pyridine-2,3-diamine

A mixture of 5-bromo-N-(cyclopropylmethyl)-3-nitropyridin-2-amine (Step C, 5.5 g, 20.3 mmol) and 3% platinum on sulfide carbon (N.E.CHEMCAT, 1 g) in methanol (250 mL) was stirred at room temperature for 3 h under hydrogen. The mixture was filtered through a pad of celite and the filtrate was concentrated to afford the title compound (4.9 g, 100%) as black oil.

$^1$H-NMR (CDCl$_3$) δ: 7.76 (d, J=2.0 Hz, 1H), 6.97 (d, J=2.0 Hz, 1H), 4.25 (br, 1H), 3.29 (br s, 2H), 3.23 (d, J=6.6 Hz, 2H), 1.18-1.07 (m, 1H), 0.58-0.51 (m, 2H), 0.29-0.23 (m, 2H). MS (ESI) 242 (M+H)$^+$.

Step E. N-{5-Bromo-2-[(cyclopropylmethyl)amino]pyridin-3-yl}-3,3-dimethylbutanamide The title compound was prepared according to the procedure described in Step C of Example 1 using 5-bromo-N$^2$-(cyclopropylmethyl)pyridine-2,3-diamine (Step D) instead of 4-bromo-N$^1$-(cyclopropylmethyl)benzene-1,2-diamine.

$^1$H-NMR (CDCl$_3$) δ: 8.08 (d, J=2.0 Hz, 1H), 7.57 (d, J=2.0 Hz, 1H), 6.74 (br, 1H), 4.67 (br, 1H), 3.22 (dd, J=6.9, 4.9 Hz, 2H), 2.29 (s, 2H), 1.15 (s, 9H), 1.11-1.01 (m, 1H), 0.57-0.50 (m, 2H), 0.28-0.22 (m, 2H). MS (ESI) 340 (M+H)$^+$, 338 (M−H)$^−$.

Step F. 6-Bromo-3-(cyclopropylmethyl)-2-(2,2-dimethylpropyl)-3H-imidazo[4,5-b]pyridine A mixture of N-{5-bromo-2-[(cyclopropylmethyl)amino]pyridin-3-yl}-3,3-dimethylbutanamide (5.04 g, 14.8 mmol, step E) and 2 N sodium hydroxide solution (10 mL) in ethanol (90 mL) was stirred under reflux for 21 h. After concentration, the residue was dissolved in water (50 mL) and the mixture was extracted with ethyl acetate (30 mL×2). The organic extracts were dried over sodium sulfate and concentrated. The residue was purified by column chromatography on silica gel (hexane:ethyl acetate=9:1 as eluent) to give the title compound (3.9 g, 82%) as a pale pink solid.

$^1$H-NMR (CDCl$_3$) δ: 8.34 (d, J=2.0 Hz, 1H), 8.10 (d, J=2.0 Hz, 1H), 4.17 (d, J=7.3 Hz, 2H), 2.85 (s, 2H), 1.33-1.19 (m, 1H), 1.10 (s, 9H), 0.57-0.43 (m, 4H). MS (ESI) 322 (M+H)$^+$.

Step G. Methyl {[3-(cyclopropylmethyl)-2-(2,2-dimethylpropyl)-3H-imidazo[4,5-b]pyridin-6-yl]thio}acetate The title compound was prepared according to the procedure described in Step E Example 1 using 6-bromo-3-(cyclopropylmethyl)-2-(2,2-dimethylpropyl)-3H-imidazo[4,5-b]pyridine (Step F) instead of 5-bromo-1-(cyclopropylmethyl)-2-(2,2-dimethylpropyl)-1H-benzimidazole.

$^1$H-NMR (CDCl$_3$) δ: 8.43 (d, J=2.2 Hz, 1H), 8.15 (d J=2.2 Hz, 1H), 4.18 (d, J=6.6 Hz, 2H), 3.71 (s, 3H), 3.59 (s, 2H), 2.86 (s, 2H), 1.31-1.19 (m, 1H), 1.11 (s, 9H), 0.58-0.50 (m, 2H), 0.50-0.46 (m, 2H). MS (ESI) 348 (M+H)$^+$.

Step H. Methyl {[3-(cyclopropylmethyl)-2-(2,2-dimethylpropyl)-3H-imidazo[4,5-b]pyridin-6-yl]sulfonyl}acetate To a solution of Methyl {[3-(cyclopropylmethyl)-2-(2,2-dimethylpropyl)-3H-imidazo[4,5-b]pyridin-6-yl]thio}acetate (Step G, 1.64 g, 4.72 mmol) in dichloromethane (30 mL) was added trifluoroacetic acid (0.7 mL, 9.44 mmol) and m-chloroperbenzoic acid (2.4 g, 14.2 mmol) portionwise at 0° C. The mixture was allowed to warm to room temperature for 3 h. The mixture was quenched with sodium sulfite aqueous solution and extracted with dichloromethane (50 mL). The organic layer was washed with saturated sodium hydrogencarbonate aqueous solution, dried over sodium sulfate and concentrated under reduced pressure. The residue was purified by silica gel column chromatography (hexane:ethyl acetate=2:1 as eluent) to afford the title compound (1.54 g, 86%) as a orange viscous oil.

$^1$H-NMR (CDCl$_3$) δ: 8.85 (d, J=1.5 Hz, 1H), 8.49 (d J=2.2 Hz, 1H), 4.25 (d, J=7.3 Hz, 2H), 4.20 (s, 2H), 3.75 (s, 3H), 2.91 (s, 2H), 1.30-1.21 (m, 1H), 1.13 (s, 9H), 0.62-0.47 (m, 4H). MS (ESI) 380 (M+H)$^4$, 378 (M−H)$^−$.

Step I. Methyl 2-{[3-(cyclopropylmethyl)-2-(2,2-dimethylpropyl)-3H-imidazo[4,5-b]pyridin-6-yl]sulfonyl}-2-methylpropanoate The title compound was prepared according to the procedure described in Step G Example 1 using methyl {[3-(cyclopropylmethyl)-2-(2,2-dimethylpropyl)-3H-imidazo[4,5-b]pyridin-6-yl]sulfonyl}acetate (Step H) instead of methyl {[1-(cyclopropylmethyl)-2-(2,2-dimethylpropyl)-1H-benzimidazol-5-yl]sulfonyl}acetate.

$^1$H-NMR (CDCl$_3$) δ: 8.72 (d, J=1.5 Hz, 1H), 8.40 (d J=1.5 Hz, 1H), 4.24 (d, J=7.3. Hz, 2H), 3.74 (s, 3H), 2.91 (s, 2H), 1.67 (s, 6H), 1.30-1.22 (m, 1H), 1.14 (s, 9H), 0.63-0.47 (m, 4H). MS (ESI) 408 (M+H)$^+$.

Step J. 2-{[3-(Cyclopropylmethyl)-2-(2,2-dimethylpropyl)-3H-imidazo[4,5-b]pyridin-6-yl]sulfonyl}-2-methylpropanoic Acid The title compound was prepared according to the procedure described in Step H Example 1 using methyl 2-{[3-(cyclopropylmethyl)-2-(2,2-dimethylpropyl)-3H-imidazo[4,5-b]pyridin-6-yl]sulfonyl}-2-methylpropanoate (Step I) instead of methyl 2-{[1-(cyclopropylmethyl)-2-(2,2-dimethylpropyl)-1H-benzimidazol-5-yl]sulfonyl}-2-methylpropanoate.

$^1$H-NMR (CDCl$_3$) δ: 8.92 (d, J=2.2 Hz, 1H), 8.89 (d, J=2.2 Hz, 1H), 4.25 (d, J=7.3 Hz, 2H), 2.92 (s, 2H), 1.73 (s, 6H), 1.26-1.19 (m, 1H), 1.05 (s, 9H), 0.61-0.45 (m, 4H), a peak of COOH was not observed. MS (ESI) 394 (M+H)$^+$.

Step K. 2-{[3-(Cyclopropylmethyl)-2-(2,2-dimethylpropyl)-3H-imidazo[4,5-b]pyridin-6-yl]sulfonyl}-2-methylpropanamide The title compound was prepared according to the procedure described in Step I of Example 1 using 2-{[3-(cyclopropylmethyl)-2-(2,2-dimethylpropyl)-3H-imidazo[4,5-b]pyridin-6-yl]sulfonyl}-2-methylpropanoic acid (Step J) instead of 2-{[1-(cyclopropylmethyl)-2-(2,2-dimethylpropyl)-1H-benzimidazol-5-yl]sulfonyl}-2-methylpropanoic acid.

$^{1}$H-NMR (CDCl$_{3}$) δ: 8.78 (d, J=2.0 Hz, 1H), 8.44 (d, J=2.0 Hz, 1H), 7.08 (br s, 1H), 5.60 (br s, 1H), 4.23 (d, J=6.6 Hz, 2H), 2.90 (s, 2H), 1.65 (s, 6H), 1.29-1.21 (m, 1H), 1.14 (s, 9H), 0.64-0.46 (m, 4H). MS (ESI) 393 (M+H)$^{+}$.

Example 6

1-(Cyclopropylmethyl)-5-[(1,1-dimethyl-2-morpholin-4-yl-2-oxoethyl)sulfonyl]-2-(2,2-dimethylpropyl)-1H-benzimidazole

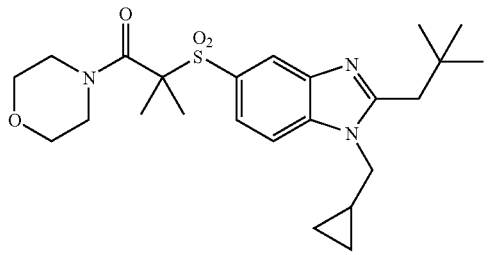

To a solution of 2-{[1-(cyclopropylmethyl)-2-(2,2-dimethylpropyl)-1H-benzimidazol-5-yl]sulfonyl}-2-methylpropanoic acid (Example 1, Step H, 180 mg, 0.46 mmol), morpholine (Wako Pure Chemical Industries, Ltd., 48 mg, 0.55 mmol), N,N'-diisopropylethylamine (71 mg, 0.55 mmol) in N,N'-dimethylformamide (3 mL) was added diethyl cyanophosphonate (Aldrich, 90 mg, 0.55 mmol) at room temperature. The mixture was stirred at room temperature for 20 h and concentrated under reduced pressure. The residue was purified by column chromatography on silica gel (hexane:ethyl acetate=1:4 as eluent) to afford the title compound (102 mg, 48%) as a white solid.

$^{1}$H-NMR (CDCl$_{3}$) δ: 8.25 (d, J=1.3 Hz, 1H), 7.70 (dd, J=8.6, 1.3 Hz, 1H), 7.47 (d, J=8.6 Hz, 1H), 4.11 (d, J=6.6 Hz, 2H), 3.96-3.76 (m, 8H), 2.85 (s, 2H), 1.69 (s, 6H), 1.27-1.14 (m, 1H), 1.10 (s, 9H), 0.68-061 (m, 2H), 0.43-0.37 (m, 2H). MS (ESI) m/z 462 (M+H)$^{+}$.

Example 7

2-{[1-(Cyclopropylmethyl)-2-(2,2-dimethylpropyl)-1H-benzimidazol-5-yl]sulfonyl}-N,N,2-trimethylpropanamide

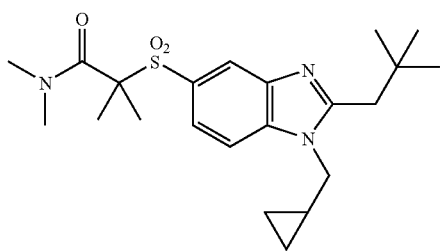

Step A. 2-{[1-(Cyclopropylmethyl)-2-(2,2-dimethylpropyl)-1H-benzimidazol-5-yl]sulfonyl}-2-methylpropanoyl Chloride Hydrochloride A mixture of 2-{[1-(cyclopropylmethyl)-2-(2,2-dimethylpropyl)-1H-benzimidazol-5-yl]sulfonyl}-2-methylpropanoic acid (Step H of Example 1, 150 mg, 0.38 mmol) and thionyl chloride (4 mL) was stirred at reflux temperature. After 3 h, the mixture was concentrated under reduced pressure to afford the title compound (175 mg, quant).

$^{1}$H-NMR (300 MHz, CDCl$_{3}$) δ: 8.60 (s, 1H), 8.00 (d, J=7.5 Hz, 1H), 7.87 (d, J=7.5 Hz, 1H), 4.26-4.40 (m, 2H), 3.33 (s, 2H), 1.78 (s, 6H), 1.41-1.10 (m, 1H), 1.21 (s, 9H), 0.92-0.75 (m, 2H), 0.66-0.40 (m, 2H).

Step B. 2-{[1-Cyclopropylmethyl)-2-(2,2-dimethylpropyl)-1H-benzimidazol-5-yl]sulfonyl}-N,N,2-trimethylpropanamide To a solution of dimethylamine (2 mol/L tetrahydrofurane solution, 0.950 mL, 1.90 mmol) in dichloromethane (3 mL) was added 2-{[1-(cyclopropylmethyl)-2-(2,2-dimethylpropyl)-1H-benzimidazol-5-yl]sulfonyl}-2-methylpropanoyl chloride hydrochloride (Step A, 175 mg, 0.380 mmol) in dichloromethane (2 mL) at room temperature. After stirring at the same temperature for 1.5 h, the mixture was diluted with dichloromethane. The whole was washed with saturated sodium hydrogencarbonate aqueous solution, dried over magnesium sulfate and concentrated under reduced pressure. The residue was purified by HPLC (ODS, gradient elution with acetonitrile/0.01% aq. NH$_{3}$=4:96 to 96:4, by volume; flow rate 40 mL/min) to afford the title compound (75 mg, 47%) as an amorphous.

$^{1}$H-NMR (300 MHz, DMSO-d$_{6}$) δ: 7.94 (s, 1H), 7.83 (d, J=7.5 Hz, 1H), 7.57 (d J=7.5 Hz, 1H), 4.24 (d, J=6.0 Hz, 2H), 3.06 (br, 6H), 2.86 (s, 2H), 1.58 (s, 6H), 1.28-1.14 (m, 1H), 1.07 (s, 9H), 0.54-0.42 (m, 4H). MS (ESI) m/z 420 (M+H)$^{+}$.

Example 8

2-{[1-(Cyclopropylmethyl)-2-(2,2-dimethylpropyl)-1H-benzimidazol-5-yl]sulfonyl}-N,2-dimethylpropanamide

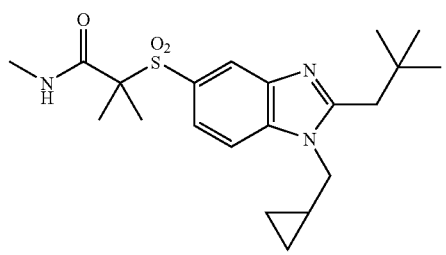

The title compound was prepared according to the procedure described in Step B of Example 7 using methylamine (40% aqueous solution) instead of dimethylamine.

$^{1}$H-NMR (300 MHz, CDCl$_{3}$) δ: 8.24 (s, 1H), 7.68 (d, J=9.0 Hz, 1H), 7.47 (d J=9.0 Hz, 1H), 7.21 (br, 1H), 4.11 (d, J=6.0 Hz, 2H), 2.90 (d, J=4.5 Hz, 3H), 2.85 (s, 2H), 1.60 (s, 6H), 1.34-1.04 (m, 1H), 1.10 (s, 9H), 0.73-0.57 (m, 2H), 0.48-0.32 (m, 2H). MS (ESI) m/z 406 (M+H)$^{+}$.

Example 9

2-{[1-(Cyclopropylmethyl)-2-(2,2-dimethylpropyl)-1H-benzimidazol-5-yl]sulfonyl}-N-(2-hydroxyethyl)-2-methylpropanamide

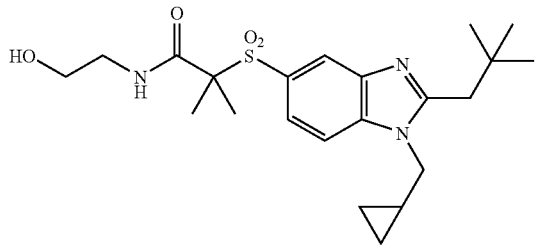

To a mixture of ethanolamine (54 mg, 0.886 mmol), triethylamine (0.184 mL, 1.32 mmol) and dichloromethane (3 mL) was added a solution of 2-{[1-(cyclopropylmethyl)-2-(2,2-dimethylpropyl)-1H-benzimidazol-5-yl]sulfonyl}-2-methylpropanoyl chloride hydrochloride (Step A of Example 7, 198 mg, 0.443 mmol) in dichloromethane (2 mL) at room temperature. After stirring at the same temperature for 1 h, the mixture was concentrated under reduced pressure. The residue was purified by HPLC (ODS, gradient elution with acetonitrile/0.01% aq. $NH_3$=4:96 to 96:4, by volume; flow rate 40 mL/min) to afford the title compound (105 mg, 55%) as an amorphous.

$^1$H-NMR (300 MHz, $CDCl_3$) δ: 8.43 (s, 1H), 7.74 (d, J=7.5 Hz, 1H), 7.59 (br, 1H), 7.48 (d J=7.5 Hz, 1H), 4.11 (d, J=6.0 Hz, 2H), 3.83-3.70 (m, 2H), 3.59-3.41 (m, 2H), 3.17 (br, 1H), 2.84 (s, 2H), 1.62 (s, 6H), 1.29-1.05 (m, 1H), 1.09 (s, 9H), 0.75-0.59 (m, 2H), 0.48-0.32 (m, 2H). MS (ESI) m/z 436 $(M+H)^+$.

Example 10

N-(2-Amino-2-oxoethyl)-2-{[1-(cyclopropylmethyl)-2-(2,2-dimethylpropyl)-1H-benzimidazol-5-yl]sulfonyl}-N-(2-hydroxyethyl)-2-methylpropanamide

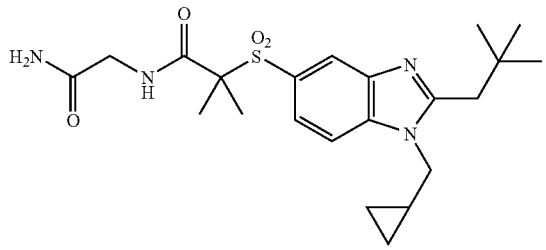

The title compound was prepared according to the procedure described in Example 9 using 2-aminoacetamide hydrochloride instead of ethanolamine.

$^1$H-NMR (300 MHz, $CDCl_3$) δ: 8.27 (s, 1H), 7.74 (d, J=7.5 Hz, 1H), 7.56 (t, J=6.0 Hz, 1H), 7.51 (d J=7.5 Hz, 1H), 6.50 (br, 1H), 5.52 (br, 1H), 4.12 (d, J=6.0 Hz, 2H), 4.06 (d, J=6.0 Hz, 2H), 2.86 (s, 2H), 1.59 (s, 6H), 1.26-0.97 (m, 1H), 1.11 (s, 9H), 0.74-0.58 (m, 2H), 0.48-0.31 (m, 2H). MS (ESI) m/z 449 $(M+H)^+$, 447 $(M-H)^-$.

Example 11

N-(2-Aminoethyl)-2-{[1-(cyclopropylmethyl)-2-(2,2-dimethylpropyl)-1H-benzimidazol-5-yl]sulfonyl}-N-(2-hydroxyethyl)-2-methylpropanamide

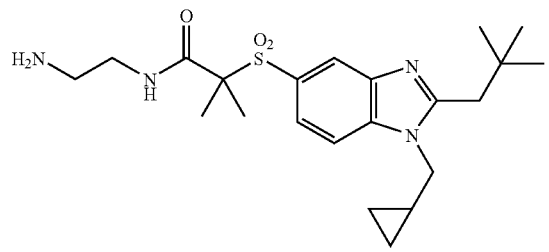

Step A. 1,1-Dimethylethyl {2-[(2-{[1-(Cyclopropylmethyl)-2-(2,2-dimethylpropyl)-1H-benzimidazol-5-yl]sulfonyl}-2-methylpropanoyl)amino]ethyl}carbamate The title compound was prepared according to the procedure described in Example 9 using tert-butyl N-(2-aminoethyl)carbamate instead of ethanolamine. MS (ESI) m/z 535 $(M+H)^+$.

Step B. N-(2-Aminoethyl)-2-{[1-(cyclopropylmethyl)-2-(2,2-dimethylpropyl)-1H-benzimidazol-5-yl]sulfonyl}-N-(2-hydroxyethyl)-2-methylpropanamide A mixture of 1,1-dimethylethyl {2-[(2-{[1-(cyclopropylmethyl)-2-(2,2-dimethylpropyl)-1H-benzimidazol-5-yl]sulfonyl}-2-methylpropanoyl)amino]ethyl}carbamate (Step A, 217 mg, 0.406 mmol) and trifluoroacetic acid (4 mL) was stirred at room temperature for 1 h. After the mixture was concentrated under reduced pressure, the residue was diluted with dichloromethane. The mixture was washed with 2 mol/L sodium hydroxide aqueous solution and brine, dried over sodium sulfate and concentrated under reduced pressure. The crude product was purified by HPLC (ODS, gradient elution with acetonitrile/0.01% aq. $NH_3$=4:96 to 96:4, by volume; flow rate 40 mL/min) to afford the title compound (127 mg, 71%) as an amorphous.

$^1$H-NMR (300 MHz, $CDCl_3$) δ: 8.30 (s, 1H), 7.73 (d, J=9.0 Hz, 1H), 7.48 (br, 1H), 7.47 (d J=9.0 Hz, 1H), 4.11 (d, J=9.0 Hz, 2H), 3.38 (dt, J=6.0, 6.0 Hz, 2H), 2.92 (t, J=6.0 Hz, 2H), 2.85 (s, 2H), 1.60 (s, 6H), 1.42-1.02 (m, 1H), 1.10 (s, 9H), 0.76-0.58 (m, 2H), 0.47-0.33 (m, 2H), a peak of $NH_2$ was not identified. MS (ESI) m/z 435 $(M+H)^+$.

Example 12

2-({2-tert-Butyl-1-[(1-hydroxycyclopentyl)methyl]-1H-benzimidazol-5-yl}sulfonyl)-2-methylpropanamide

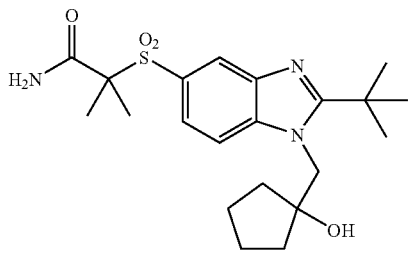

Step A. 1-{[(4-Bromo-2-nitrophenyl)amino]methyl}cyclopentanol

A mixture of 2,5-dibromonitrobenzene Tokyo Kasei Kogyo Co., Ltd., 5.4 g, 19.2 mmol), 1-(aminomethyl)cyclopentanol hydrochloride (*J. Med. Chem.* 1981, 24, 12-16, 4.3 g, 28.4 mmol) and N,N'-diisopropylethylamine (8.4 mL, 48.1 mmol) in 1-methyl-2-pyrrolidinone (32 mL) was subjected in Microwave oven for 30 ml at 200° C. The reaction was quenched with water and extracted three times with ethyl acetate. The combined organic layers were dried over sodium sulfate and filtered. The filtrate was concentrated and the residue was purified by column chromatography on silica gel (hexane:ethyl acetate=5:1 as eluent) to afford the title compound (2.6 g, 43%) as an orange amorphous.

$^1$H-NMR (CDCl$_3$) δ:8.36 (br s, 1H), 8.32 (d, J=2.2 Hz, 1H), 7.49 (dd, J=8.8, 2.2 Hz, 1H), 6.83 (d, J=9.5 Hz, 1H), 3.40 (d, J=5.1 Hz, 2H), 1.96-1.67 (m, 8H), a peak of OH was not identified. MS (ESI) 315 (M+H)$^+$, 313 (M–H)$^-$.

Step B. 1-{[(2-Amino-4-bromophenyl)amino]methyl}cyclopentanol

The title compound was prepared according to the procedure described in Step B of Example 1 using 1-{[(4-bromo-2-nitrophenyl)amino]methyl}cyclopentanol (Step A) instead of 4-bromo-N-(cyclopropylmethyl)-2-nitroaniline.

$^1$H-NMR (CDCl$_3$) δ:6.89 (dd, J=8.8, 2.2 Hz, 1H), 6.84 (d, J=2.2 Hz, 1H), 6.54 (d, J=8.1, 1H), 3.50 (br s, 2H), 3.14 (s, 2H), 1.95-1.62 (m, 8H), peaks of OH and NH were not identified. MS (ESI) 285 (M+H)$^+$.

Step C N-(5-Bromo-2-{[(1-hydroxycyclopentyl)methyl]amino}phenyl)-2,2-dimethylpropanamide To a solution of 1-([(2-amino-4-bromophenyl)amino]methyl)cyclopentanol (Step B, 1.3 g, 4.15 mmol) in ethyl acetate (100 mL) was added pivaloyl chloride (511 mg, 4.15 mmol) at room temperature. After stirring for 2 h at room temperature, the mixture was quenched with saturated sodium hydrogen carbonate aqueous solution. The mixture was extracted with ethyl acetate. The combined organic layers were dried over sodium sulfate and concentrated. The residue was purified by column chromatography on silica gel (hexane:ethyl acetate=5:1 as eluent) to afford the title compound (1.3 g, 75%) as a beige amorphous.

$^1$H-NMR (CDCl$_3$) δ:7.43 (d, J=2.2 Hz, 1H), 7.31 (br s, 1H), 7.22 (dd, J=8.1, 2.2 Hz, 1H), 6.69 (d, J=8.8 Hz, 1H), 4.07 (br s, 1H), 3.17 (d, J=3.7 Hz, 2H), 2.12 (s, 1H), 1.93-1.61 (m, 8H), 1.34 (s, 9H). MS (ESI) 371 (M+H)$^+$, 369 (M–H)$^-$.

Step D. 1-[(5-Bromo-2-tert-butyl-1H-benzimidazol-1-yl)methyl]cyclopentanol

To a solution of N-(5-bromo-2-{[(1-hydroxycyclopentyl)methyl]amino}phenyl)-2,2-dimethylpropanamide (Step C, 1.3 g, 3.41 mmol) in toluene (100 mL) was added p-toluenesulfonic acid monohydrate (130 mg, 0.68 mmol) at room temperature and the mixture was stirred at 140° C. for 23 h. After cooling to room temperature, p-toluenesulfonic acid monohydrate (130 mg, 0.68 mmol) was added, and the mixture was heated at 140° C. After stirring for 26 h at 140° C., the mixture was quenched with saturated sodium hydrogen carbonate aqueous solution. The mixture was extracted with ethyl acetate. The combined organic layers were dried over sodium sulfate and concentrated. The residue was purified by column chromatography on silica gel (hexane:ethyl acetate:dichloromethane=5.5:1:0.5 as eluent) to afford the title compound (453 mg, 38%) as a beige amorphous.

$^1$H-NMR (CDCl$_3$) δ:7.88 (d, J=2.2 Hz, 1H), 7.43 (d, J=8.8 Hz, 1H), 7.30 (dd, J=8.8, 2.2 Hz, 1H), 4.55 (s, 2H), 1.88-1.69 (m, 8H), 1.57 (s, 9H), 1.22 (s, 1H). MS (ESI) 353 (M+H)$^+$.

Step E. Methyl ({2-tert-butyl-1-[(1-hydroxycyclopentyl)methyl]-1H-benzimidazol-5-yl}thio)acetate The title compound was prepared according to the procedure described in Step E of Example 1 using 1-[(5-bromo-2-tert-butyl-1H-benzimidazol-1-yl)methyl]cyclopentanol (Step D) instead of 5-bromo-1-(cyclopropylmethyl)-2-(2,2-dimethylpropyl)-1H-benzimidazole.

$^1$H-NMR (CDCl$_3$) δ:7.86 (d, J=1.5 Hz, 1H), 7.49 (d, J=8.8 Hz, 1H), 7.33 (dd, J=8.8, 1.5 Hz, 1H), 4.55 (s, 2H), 3.71 (s, 3H), 3.63 (s, 2H), 1.89-1.70 (m, 8H), 1.57 (s, 9H), 1.24 (s, 1H). MS (ESI) 377 (M+H)$^+$.

Step F. Methyl ({2-tert-butyl-1-[(1-hydroxycyclopentyl)methyl]-1H-benzimidazol-5-yl}sulfonyl)acetate The title compound was prepared according to the procedure described in Step F of Example 1 using methyl ({2-tert-butyl-1-[(1-hydroxycyclopentyl)methyl]-1H-benzimidazol-5-yl}thio)acetate (Step E) instead of methyl ([1-(cyclopropylmethyl)-2-(2,2-dimethylpropyl)-1H-benzimidazol-5-yl]thio)acetate.

$^1$H-NMR (CDCl$_3$) δ:8.35 (s, 1H), 7.78 (br s, 2H), 4.63 (s, 2H), 4.15 (s, 2H), 3.72 (s, 3H), 1.90-1.70 (m, 8H), 1.60 (s, 9H), a peak of OH was not identified. MS (ESI) 409 (M+H)$^+$, 369 (M–H)$^-$.

Step G. Methyl 2-({2-tert-butyl 1-[(1-hydroxycyclopentyl)methyl]-1H-benzimidazol-5-yl}sulfonyl)-2-methylpropanoate The title compound was prepared according to the procedure described in Step G of Example 1 using methyl ({2-tert-butyl-1-[(1-hydroxycyclopentyl)methyl]-1H-benzimidazol-5-yl}sulfonyl)acetate (Step F) instead of methyl {[1-(cyclopropylmethyl)-2-(2,2-dimethylpropyl)-1H-benzimidazol-5-yl]sulfonyl}acetate.

$^1$H-NMR (CDCl$_3$) δ:8.26 (d, J=1.5 Hz, 1H), 7.73 (d, J=8.8 Hz, 1H), 7.65 (dd, J=8.8, 1.5 Hz, 1H), 4.62 (s, 2H), 3.72 (s, 3H), 1.88-1.70 (m, 8H), 1.63 (s, 6H), 1.60 (s, 9H), 1.35 (s, 1H). MS (ESI) 437 (M+H)$^+$.

Step H. 2-({2-tert-butyl-1-[(1-hydroxycyclopentyl)methyl]-1H-benzimidazol-5-yl}sulfonyl)-2-methylpropanecarboxylic Acid The title compound was prepared according to the procedure described in Step H of Example 1 using methyl 2-({2-tert-butyl-1-[(1-hydroxycyclopentyl)methyl]-1H-benzimidazol-5-yl}sulfonyl)-2-methylpropanoate (Step G) instead of methyl 2-{[1-(cyclopropylmethyl)-2-(2,2-dimethylpropyl)-1H-benzimidazol-5-yl]sulfonyl}-2-methylpropanoate. MS (ESI) m/z 423 (M+H)⁺

Step I. 2-({2-tert-Butyl-1-[(1-hydroxycyclopentyl)methyl]-1H-benzimidazol-5-yl}sulfonyl)-2-methylpropanamide The title compound was prepared according to the procedure described in Step I of Example 1 using 2-({2-tert-butyl-1-[(1-hydroxycyclopentyl)methyl]-1H-benzimidazol-5-yl}sulfonyl)-2-methylpropanecarboxylic acid (Step A) instead of 2-{[1-(cyclopropylmethyl)-2-(2,2-dimethylpropyl)-1H-benzimidazol-5-yl]sulfonyl}-2-methylpropanoic acid.

¹H-NMR (300 MHz, CDCl₃) δ: 8.30 (s, 1H), 7.83-7.58 (m, 2H), 7.19 (br, 1H), 5.60 (br, 1H), 4.62 (s, 2H), 1.96-1.49 (m, 8H), 1.61 (s, 6H), 1.59 (s, 9H), 1.38 (br, 1H). MS (ESI) m/z 422 (M+H)⁺.

Example 13

N-(2-{[1-(Cyclopropylmethyl)-2-(2,2-dimethylpropyl)-1H-benzimidazol-5-yl]sulfonyl}-2-methylpropyl)acetamide

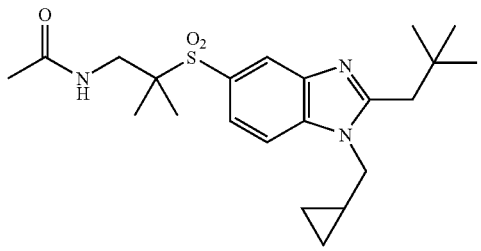

Step A. 4-Bromo-N-(cyclopropylmethyl)-2-nitroaniline

A mixture of 4-bromo-1-fluoro-2-nitrobenzene (10.3 g, 46.9 mmol), cyclopropanemethylamine (5.0 g, 70.3 mmol) and N,N'-diisopropylethylamine (15.1 g, 117 mmol) in ethanol (116 mL) was stirred at reflux temperature for 15 h. After cooling to room temperature, the mixture was concentrated under reduced pressure. The residue was purified by column chromatography on silica gel (ethyl acetate as eluent) to afford the title compound (12.7 g, quant.) as an orange solid.

¹H-NMR (CDCl₃) δ: 8.32 (d, J=2.4 Hz, 1H), 8.11 (br., 1H), 7.49-7.46 (m, 1H), 6.72 (d, J=9.2 Hz, 1H), 3.16-3.11 (m, 2H), 1.20-1.14 (m, 1H), 0.69-0.62 (m, 2H), 0.35-0.29 (m, 2H). MS (ESI) 271 (M+H)⁺.

Step B. 4-Bromo-N¹-(cyclopropylmethyl)benzene-1,2-diamine

A mixture of 4-bromo-N-(cyclopropylmethyl)-2-nitroaniline (Step A, 12.7 g, 47.0 mmol), iron powder (13.1 g, 470 mmol) and ammonium chloride (250 mg, 4.70 mmol) in ethanol (126 mL) and water (42 mL) was stirred at reflux temperature for 3 h. After cooling to room temperature, the mixture was filtered and the filtrate was concentrated under reduced pressure. The residue was dissolved in ethyl acetate (100 mL) and water (50 mL). The organic layer was separated, washed with brine (20 mL), dried over magnesium sulfate and concentrated to afford the title compound (11.3 g, 99%) as brown oil.

¹H-NMR (CDCl₃) δ: 6.88 (dd, J=8.4, 2.2 Hz, 1H), 6.83 (d, J=2.2 Hz, 1H), 6.47 (d, J=8.4 Hz, 1H), 3.41 (br., 3H), 2.90 (d, J=6.8 Hz, 1H), 1.19-1.06 (m, 1H), 0.60-0.54 (m, 2H), 0.27-0.22 (m, 2H). MS (ESI) 241 (M+H)⁺.

Step C. N-{5-Bromo-2-[(cyclopropylmethyl)amino]phenyl}-3,3-dimethylbutanamide

To a solution of 4-bromo-N¹-(cyclopropylmethyl)benzene-1,2-diamine (Step B, 11.3 g, 46.9 mmol) and N,N-diisopropylethylamine (6.06 g, 46.9 mmol) in ethyl acetate (88 mL) was added tert-butylacetyl chloride (6.31 g, 46.9 mmol) at 0° C. and the mixture was allowed to warm to room temperature for 15 h. The reaction mixture was washed with saturated sodium hydrogen carbonate aqueous solution (100 mL×2), brine (50 mL). The resulting ethyl acetate solution of reaction mixture was dried over magnesium sulfate and concentrated under reduced pressure. The crude product was washed with ethyl acetate to afford the title compound (11.2 g, 70%) as a white solid.

¹H-NMR (CDCl₃) δ: 7.42 (d, J=2.0 Hz, 1H), 7.21 (dd, J=8.6, 2.0 Hz, 1H), 6.97 (br., 1H), 6.59 (d, J=8.6 Hz, 1H), 3.95 (br., 1H), 2.89 (d, J=7.1 Hz, 2H), 2.28 (s, 2H), 1.14-0.98 (m, 10H), 0.61-0.52 (m, 2H), 0.27-0.21 (m, 2H), MS (ESI) 339 (M+H)⁺, 337 (M−H)⁻.

Step D. 5-Bromo-1-(cyclopropylmethyl)-2-(2,2-dimethylpropyl)-1H-benzimidazole

A mixture of N-{5-bromo-2-[(cyclopropylmethyl)amino]phenyl}-3,3-dimethylbutanamide (Step C, 11.2 g, 33.0 mmol), p-toluenesulfonic acid monohydrate (6.29 g, 33.0 mmol) and toluene (240 mL) was stirred at reflux temperature for 20 h with Dean-Stark apparatus. The mixture was cooled to 0° C. The resulting precipitate was collected by filtration and washing with small amount of ethyl acetate. The residue was dissolved in ethyl acetate (200 mL). The whole was extracted with saturated sodium hydrogen carbonate aqueous solution (100 mL). The organic layer was washed with brine (20 mL), dried over magnesium sulfate and concentrated under reduced pressure. The residue was purified by column chromatography on silica gel (hexane:ethyl acetate=3:1 as eluent) to give the title compound (10.1 g, 95%) as a white solid.

¹H-NMR (CDCl₃) δ: 7.88 (d, J=1.8 Hz, 1H), 7.33 (dd, J=8.5, 1.8 Hz, 1H), 7.22 (d, J=8.5 Hz, 1H), 4.05 (d, J=7.2 Hz, 2H), 2.80 (s, 2H), 1.19-1.10 (m, 1H), 1.07 (s, 9H), 0.63-0.57 (m, 2H), 0.38-0.33 (m, 2H). MS (ESI) 321 (M+H)⁺.

Step E. Methyl {[1-(cyclopropylmethyl)-2-(2,2-dimethylpropyl)-1H-benzimidazol-5-yl]thio}acetate To a solution of 5-bromo-1-(cyclopropylmethyl)-2-(2,2-dimethylpropyl)-1H-benzimidazole (Step D, 4.0 g, 12.5 mmol) in 1,4-dioxane (25 mL) were added N,N'-diisopropylethylamine (4.4 mL, 25 mmol), methyl mercaptoacetate (1.1 ml, 12.5 mmol), tris(dibenzylideneacetone)dipalladium(0) (284 mg, 0.31 mmol) and 4,5-bis(diphenylphosphino)-9,9-dimethylxanthene (362 mg, 0.63 mmol). The mixture was stirred at reflux temperature for 24 h under nitrogen atmosphere. After cooling to room temperature, the mixture was filtered and the filtrate was concentrated under reduced pressure. The residue was purified by column chromatography on silica gel (hexane:ethyl acetate=2:1 as eluent) to afford the title compound (4.75 g, quant.) as a pale yellow oil.

¹H-NMR (CDCl₃) δ: 7.88 (d, J=1.5 Hz, 1H), 7.37 (dd, J=8.1, 1.5 Hz, 1H), 7.30 (d, J=8.1 Hz, 1H), 4.05 (d, J=6.6 Hz, 2H), 3.71 (s, 3H), 3.64 (s, 2H), 2.81 (s, 2H), 1.22-1.13 (m, 1H), 1.08 (s, 9H), 0.63-0.57 (m, 2H), 0.39-0.34 (m, 2H). MS (ESI) 347 (M+H)⁺.

Step F. Methyl {[1-(cyclopropylmethyl)-2-(2,2-dimethylpropyl-1H-benzimidazol-5-yl]sulfonyl}acetate To a solution of methyl {[1-(cyclopropylmethyl)-2-(2,2-dimethylpropyl)-1H-benzimidazol-5-yl]thio}acetate (Step E, 4.75 g, 12.5 mmol) in dichloromethane (100 mL) was added m-chloroperbenzoic acid (6.75 g, 27.4 mmol) portionwise at 0° C. The mixture was allowed to warm to room temperature for 3 h. The mixture was quenched with sodium sulfite aqueous solution and extracted with dichloromethane (50 mL). The organic layer was washed with saturated sodium hydrogen carbonate aqueous solution, dried over sodium sulfate and concentrated under reduced pressure. The residue was purified by column chromatography on silica gel (hexane:ethyl acetate=2:1 to 1:1 as eluent) to afford the title compound (4.33 g, 91%) as a yellow solid.

$^1$H-NMR (CDCl$_3$) δ: 8.35 (br s, 1H), 7.83 (dd, J=8.8, 1.5 Hz, 1H), 7.50 (d, J=8.8 Hz, 1H), 4.17 (s, 2H), 4.12 (d, J=6.6 Hz, 2H), 3.73 (s, 3H), 2.86 (s, 2H), 1.15-1.06 (m, 10H), 0.70-0.60 (m, 2H), 0.44-0.35 (m, 2H). MS (ESI) 379 (M+H)$^+$.

Step G. Methyl 2-{[1-(cyclopropylmethyl)-2-(2,2-dimethylpropyl)-1H-benzimidazol-5-yl]sulfonyl}-2-methylpropanoate To a solution of methyl {[1-(cyclopropylmethyl)-2-(2,2-dimethylpropyl)-1H-benzimidazol-5-yl]sulfonyl}acetate (Step F, 1.0 g, 2.64 mmol) in N,N'-dimethylformamide (11.5 mL) were added sodium hydride (233 mg, 5.81 mmol) and methyl iodide (825 mg, 5.81 mmol) at 0° C. The mixture was stirred at room temperature for 15 h. The mixture was quenched with water (120 mL) and extracted with ethyl acetate (60 mL×4). The combined organic layer was washed with water (50 mL×4), brine (20 mL), dried over magnesium sulfate and concentrated under reduced pressure. The residue was purified by column chromatography on silica gel (hexane:ethyl acetate=1:1 as eluent) to afford the title compound (1.12 g, quant.) as a yellow oil.

$^1$H-NMR (CDCl$_3$) δ: 8.26 (br s, 1H), 7.71 (dd, J=8.1, 2.2 Hz, 1H), 7.46 (d, J=8.1 Hz, 1H), 4.12 (d, J=6.6 Hz, 2H), 3.71 (s, 3H), 2.85 (s, 2H), 1.65 (s, 6H), 1.20-1.03 (m, 10H), 0.71-0.57 (m, 2H), 0.46-0.32 (m, 2H). MS (ESI) 407 (M+H)$^+$.

Step H. 2-{[1-(Cyclopropylmethyl)-2-(2,2-dimethylpropyl)-1H-benzimidazol-5-yl]sulfonyl}-2-methylpropan-1-ol To a suspension of lithium aluminum hydride (46 mg, 1.22 mmol) in tetrahydrofuran (5 mL) was added a solution of methyl 2-{[1-(cyclopropylmethyl)-2-(2,2-dimethylpropyl)-1H-benzimidazol-5-yl]sulfonyl}-2-methylpropanoate (Step G, 452 mg, 1.11 mmol) in tetrahydrofuran (5 mL) at 0° C. After stirring for 3 h at 0° C., the mixture was quenched with potassium fluoride (210 mg, 3.66 mmol) and sodium sulfate decahydrate (1.57 g, 4.88 mmol) at 0° C. The resulting mixture was filtered through a pad of celite and the filtrate was concentrated under reduced pressure. The residue was purified by column chromatography on silica gel (hexane:ethyl acetate=1:1 as eluent) to afford the title compound (388 mg, 92%) as a white amorphous.

$^1$H-NMR (CDCl$_3$) δ: 8.29 (d, J=2.2 Hz, 1H), 7.75 (dd, J=8.8, 1.5 Hz, 1H), 7.49 (d J=8.8 Hz, 1H), 4.13 (d, J=-6.6 Hz, 2H), 3.76 (d, J=6.6 Hz, 2H), 3.09 (t, J=6.6 Hz, 1H), 2.86 (s, 2H), 1.34 (s, 6H), 1.17-1.07 (m, 10H), 0.71-0.60 (m, 2H), 0.45-0.35 (m, 2H). MS (ESI) 379 (M+H)$^+$.

Step I. 2-{[1-(Cyclopropylmethyl)-2-(2,2-dimethylpropyl)-1H-benzimidazol-5-yl]sulfonyl}-2-methylpropyl Methanesulfonate To a solution of 2-{[1-(cyclopropylmethyl)-2-(2,2-dimethylpropyl)-1H-benzimidazol-5-yl]sulfonyl}-2-methylpropan-1-ol (Step H, 356 mg, 0.94 mmol) in dichloromethane (8 mL) were added triethylamine (157 µL, 1.13 mmol) and methanesulfonyl chloride (87 µL, 1.13 mmol) at 0° C. The mixture was stirred at room temperature for 1 h. The reaction mixture was quenched with water (10 mL) and extracted with dichloromethane (30 mL×3). The combined organic layer was dried over sodium sulfate and concentrated under reduced pressure to afford the crude title compound (411 mg) as yellow oil.

$^1$H-NMR (CDCl$_3$) δ:8.35 (br d, 1H), 7.79 (dd, J=8.8, 2.2 Hz, 1H), 7.54 (d J=8.8 Hz, 1H), 4.38 (s, 2H), 4.16 (d, J=6.6 Hz, 2H), 3.03 (s, 3H), 2.92 (s, 2H), 1.44 (s, 6H), 1.26-1.19 (m, 1H), 1.12 (s, 9H), 0.72-0.64 (m, 2H), 0.46-0.39 (m, 2H). MS (ESI) 457 (M+H)$^+$.

Step J. 5-[(2-Azido-1,1-dimethylethyl)sulfonyl]-1-(cyclopropylmethyl)-2-(2,2-dimethylpropyl)-1H-benzimidazole To a solution of sodium azide (176 mg, 2.70 mmol) in N,N'-dimethylformamide (5 mL) was added 2-{[1-(cyclopropylmethyl)-2-(2,2-dimethylpropyl)-1H-benzimidazol-5-yl]sulfonyl}-2-methylpropyl methanesulfonate (Step I, 411 mg, 0.90 mmol) in N,N'-dimethylformamide (3 mL) at room temperature. The mixture was stirred at 160° C. for 24 h. The mixture was washed with ethyl acetate (20 mL×3) and water (30 mL). The combined organic layer was dried over sodium sulfate and concentrated under reduced pressure. The residue was purified by column chromatography on silica gel (hexane:ethyl acetate=5:2 as eluent) to afford the title compound (265 mg) as a white amorphous.

$^1$H-NMR (CDCl$_3$) δ:8.27 (d, J=1.5 Hz, 1H), 7.74 (dd, J=8.8, 1.5 Hz, 1H), 7.49 (d J=8.1 Hz, 1H), 4.13 (d, J=6.6 Hz, 2H), 3.63 (s, 2H), 2.86 (s, 2H), 1.39 (s, 6H), 1.27-1.17 (m, 1H), 1.11 (s, 9H), 0.70-0.62 (m, 2H), 0.45-0.37 (m, 2H). MS (ESI) 404 (M+H)$^+$.

Step K. 2-{[1-(Cyclopropylmethyl)-2-(2,2-dimethylpropyl)-1H-benzimidazol-5-yl]sulfonyl}-2-methylpropan-1-amine A mixture of 5-[(2-azido-1,1-dimethylethyl)sulfonyl]-1-(cyclopropylmethyl)-2-(2,2-dimethylpropyl)-1H-benzimidazole (Step J, 265 mg, 0.66 mmol), 10% palladium carbon (30 mg) and methanol (8 mL) was stirred at room temperature for 18 h under hydrogen atmosphere. The reaction mixture was filtered through a pad of celite and the filtrate was concentrated under reduced pressure. The residue was purified by column chromatography on silica gel (dichloromethane:methanol=15:1 as eluent) to afford the title compound (199 mg, 80%) as a white brown solid.

$^1$H-NMR (CDCl$_3$) δ:8.28 (br, 1H), 7.75 (dd, J=8.8, 1.5 Hz, 1H), 7.47 (d J=8.1 Hz, 1H), 4.12 (d, J=6.6 Hz, 2H), 2.97 (s, 2H), 2.86 (s, 2H), 1.33 (s, 6H), 1.23-1.15 (m, 1H), 1.11 (s, 9H), 0.70-0.60 (m, 2H), 0.44-0.36 (m, 2H) a peak of NH$_2$ was not identified. MS (ESI) 378 (M+H)$^+$.

Step L. N-(2-{[1-(Cyclopropylmethyl)-2-(2,2-dimethylpropyl)-1H-benzimidazol-5-yl]sulfonyl}-2-methylpropyl)acetamide To a solution of 2-{[1-(cyclopropylmethyl)-2-(2,2-dimethylpropyl)-1H-benzimidazol-5-yl]sulfonyl}-2-methylpropan-1-amine (Step K, 132 mg, 0.350 mmol) and triethylamine (98 µL, 0.700 mmol) in dichloromethane (4 mL) was added acetyl chloride (0.03 mL, 0.420 mmol) at room temperature. After stirring for 15 min, the mixture was concentrated under reduced pressure. The residue was purified by HPLC (ODS, gradient elution with Acetonitrile/0.01% aq. NH$_3$=4:96 to 96:4, by volume; flow rate 40 mL/min) to afford the title compound (113 mg, 77%) as an amorphous.

$^1$H-NMR (300 MHz, CDCl$_3$) δ: 8.26 (s, 1H), 7.72 (d, J=7.5 Hz, 1H), 7.50 (d, J=7.5 Hz, 1H), 6.67 (br, 1H), 4.13 (d, J=6.0 Hz, 2H), 3.60 (d, J=6.0 Hz, 2H), 2.86 (s, 2H), 2.08 (s, 3H), 1.32 (s, 6H), 1.25-1.06 (m, 1H), 1.11 (s, 9H), 0.72-0.59 (m, 2H), 0.48-0.32 (m, 2H). MS (ESI) m/z 420 (M+H)⁺, 418 (M−H)⁻.

Example 14

N-(2-{[1-(Cyclopropylmethyl)-2-(2,2-dimethylpropyl)-1H-benzimidazol-5-yl]sulfonyl}-2-methylpropyl)methanesulfonamide

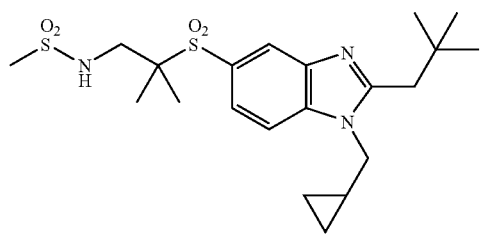

The title compound was prepared according to the procedure described in step L of Example 13 using methanesulfonyl chloride instead of acetyl chloride.

¹H-NMR (300 MHz, CDCl₃) δ: 8.26 (s, 1H), 7.73 (d, J=9.0 Hz, 1H), 7.51 (d J=9.0 Hz, 1H), 5.56 (t, J=6.0 Hz, 1H), 4.13 (d, J=6.0 Hz, 2H), 3.47 (d, J=6.0 Hz, 2H), 3.01 (s, 3H), 2.86 (s, 2H), 1.36 (s, 6H), 1.28-1.07 (m, 1H), 1.11 (s, 9H), 0.74-0.56 (m, 2H), 0.49-0.35 (m, 2H). MS (ESI) m/z 456 (M+H)⁺, 454 (M−H)⁻.

Example 15

N'-(2-{[1-(Cyclopropylmethyl)-2-(2,2-dimethylpropyl)-1H-benzimidazol-5-yl]sulfonyl}-2-methylpropyl)-N,N-dimethylurea

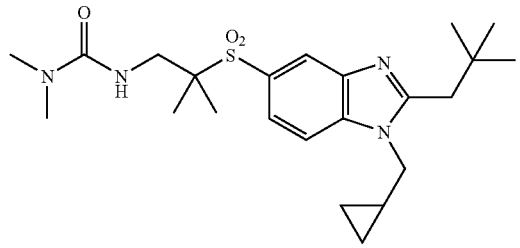

The title compound was prepared according to the procedure described in step L of Example 13 using dimethylcarbamoyl chloride instead of acetyl chloride.

¹H-NMR (300 MHz, CDCl₃) δ: 8.27 (s, 1H), 7.72 (d, J=7.5 Hz, 1H), 7.49 (d J=7.5 Hz, 1H), 5.79 (t, J=6.0 Hz, 1H), 4.13 (d, J=6.0 Hz, 2H), 3.57 (d, J=6.0 Hz, 2H), 2.97 (s, 6H), 2.86 (s, 2H), 1.33 (s, 6H), 1.30-1.15 (m, 1H), 1.11 (s, 9H), 0.72-0.58 (m, 2H), 0.50-0.31 (m, 2H). MS (ESI) m/z 449 (M+H)⁺, 447 (M−H)⁻.

Example 16

N-(2-{[1-(Cyclopropylmethyl)-2-(2,2-dimethylpropyl)-1H-benzimidazol-5-yl]sulfonyl}-2-methylpropyl)-N'-methylurea

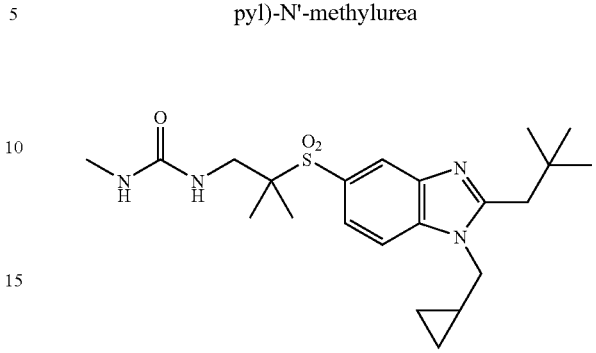

To a solution of 2-{[1-(cyclopropylmethyl)-2-(2,2-dimethylpropyl)-1H-benzimidazol-5-yl]sulfonyl}-2-methylpropan-1-amine (Step K of Example 13, 177 mg, 0.469 mmol) and triethylamine (131 μL, 0.938 mmol) in dichloromethane (4 mL) was added p-nitrophenyl chloroformate (104 mg, 0.516 mmol) at room temperature. After stirring for 30 min, methylamine (40% aqueous solution, 3 mL) was added to the mixture and the whole was stirred for 2 h. To the resulting mixture was added ethyl acetate and 2 mol/L sodium hydroxide aqueous solution. The organic layer was dried over sodium sulfate and concentrated under reduced pressure. The residue was purified by HPLC (ODS, gradient elution with Acetonitrile 10.01% aq. NH₃=4:96 to 96:4, by volume; flow rate 40 mL/min) to afford the title compound (34 mg, 17%) as an amorphous.

¹H-NMR (300 MHz, CDCl₃) δ: 8.26 (s, 1H), 7.72 (d, J=9.0 Hz, 1H), 7.49 (d J=9.0 Hz, 1H), 5.52 (t, J=6.0 Hz, 1H), 4.34 (br, 1H), 4.13 (d, J=6.0 Hz, 2H), 3.57 (d, J=6.0 Hz, 2H), 2.86 (s, 2H), 2.83 (d, J=3.0 Hz, 3H), 1.32 (s, 6H), 1.28-1.08 (m, 1H), 1.11 (s, 9H), 0.74-0.55 (m, 2H), 0.46-0.33 (m, 2H). MS (ESI) m/z 435 (M+H)⁺, 433 (M−H)⁻.

Example 17

N-(2-{[1-(Cyclopropylmethyl)-2-(2,2-dimethylpropyl)-1H-benzimidazol-5-yl]sulfonyl}-2-methylpropyl)urea

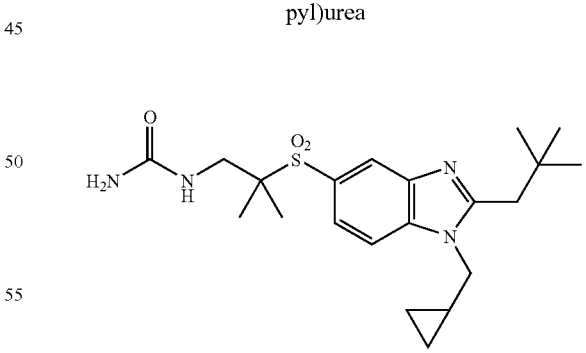

The title compound was prepared according to the procedure described in Example 16 using ammonia (25% aqueous solution) instead of methylamine.

¹H-NMR (300 MHz, CDCl₃) δ: 8.26 (s, 1H), 7.72 (d, J=9.0 Hz, 1H), 7.50 (d J=9.0 Hz, 1H), 5.69 (t, J=6.0 Hz, 1H), 4.41 (br, 2H), 4.13 (d, J=6.0 Hz, 2H), 3.56 (d, J=6.0 Hz, 2H), 2.86 (s, 2H), 1.33 (s, 6H), 1.27-1.02 (m, 1H), 1.11 (s, 9H), 0.74-0.57 (m, 2H), 0.46-0.32 (m, 2H). MS (ESI) m/z 421 (M+H)⁺, 419 (M−H)⁻.

Example 18

N-(2-{[1-(Cyclopropylmethyl)-2-(2,2-dimethylpropyl)-1H-benzimidazol-5-yl]sulfonyl}-1,1-dimethylethyl)urea

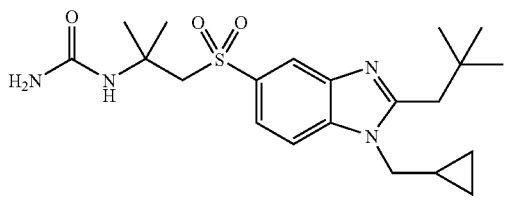

Step A. N-(Cyclopropylmethyl)-4-(methylsulfonyl)-2-nitroaniline

A mixture of 1-fluoro-4-(methylsulfonyl)-2-nitrobenzene (7.5 g, 34.2 mmol, Acros Organics), cyclopropanemethylamine (4.5 mL, 51.3 mmol) and N,N-diisopropylethylamine (9.0 mL, 51.3 mmol) was stirred at 90° C. for 18 h. The mixture was purified by column chromatography on silica gel (ethyl acetate as eluent) to afford the title compound (9.32 g, 100%) as an orange solid.

$^1$H-NMR (CDCl$_3$) δ:8.78 (d, J=2.2 Hz, 1H), 8.51 (br s, 1H), 7.89 (dd J=9.2, 2.2 Hz, 1H), 6.95 (d, J=9.2 Hz, 1H), 3.26-3.21 (m, 2H), 3.06 (s, 3H), 1.29-1.16 (m, 1H), 0.74-0.67 (m, 2H), 0.39-0.34 (m, 2H).

Step B. 2-Amino-1-(N-cyclopropylmethyamino)-4-(methylsulfonyl)benzene

A mixture of N-(cyclopropylmethyl)-4-(methylsulfonyl)-2-nitroaniline (Step A, 9.32 g, 34.2 mmol), 10% palladium carbon (950 mg), methanol (250 mL) and tetrahydrofuran (250 mL) was stirred at room temperature for 3 h under hydrogen atmosphere. The resulting mixture was filtered through a pad of celite. The filtrate was concentrated to afford the crude product (9.16 g) as brown viscous oil.

$^1$H-NMR (CDCl$_3$) δ:7.40 (dd, J=8.4, 2.1 Hz, 1H), 7.23 (d, J=2.1 Hz, 1H), 6.62 (d, J=8.4 Hz, 1H), 4.11 (br, 1H), 3.43 (br, 2H), 3.05-3.00 (m, 5H), 1.23-1.07 (m, 1H), 0.65-0.58 (m, 2H), 0.31-0.26 (m, 2H). MS (ESI) 241 (M+H)$^+$, 239 (M−H)$^-$.

Step C. N-[2-[(Cyclopropylmethyl)amino]-5-(methylsulfonyl)phenyl]-3,3-dimethylbutanamide The title compound was prepared according to the procedure described in Step C of Example 1 using 2-amino-1-(N-cyclopropylmethyamino)-4-(methylsulfonyl)benzene (Step B) instead of 4-bromo-N$^1$-(cyclopropylmethyl)benzene-1,2-diamine.

$^1$H-NMR (CDCl$_3$) δ:7.65 (dd, J=8.8, 1.5 Hz, 1H), 7.56 (d, J=2.2 Hz, 1H), 7.15 (br s, 1H), 6.69 (d, J=8.8 Hz, 1H), 4.80 (br, 1H), 3.06-2.96 (m, 5H), 2.32 (s, 2H), 1.15 (s, 9H), 1.20-1.05 (m, 1H), 0.64-0.54 (m, 2H), 0.32-0.25 (m, 2H). MS (ESI) 339 (M+H)$^+$, 337 (M−H)$^-$.

Step D. 1-(Cyclopropylmethyl)-2-(2,2-dimethylpropyl)-5-(methylsulfonyl)-1H-benzimidazole The title compound was prepared according to the procedure described in Step D of Example 1 using N-[2-[(cyclopropylmethyl)amino]-5-(methylsulfonyl)phenyl]-3,3-dimethylbutanamide (Step C) instead of N-{5-bromo-2-[(cyclopropylmethyl)amino]phenyl}-3,3-dimethylbutanamide.

$^1$H-NMR (CDCl$_3$) δ:8.35 (d, J=2.2 Hz, 1H), 7.83 (dd, J=8.8, 2.2 Hz, 1H), 7.50 (d, J=8.8 Hz, 1H), 4.13 (d, J=6.6 Hz, 2H), 3.10 (s, 3H), 2.86 (s, 2H), 1.26-1.13 (m, 1H), 1.10 (s, 9H), 0.69-0.58 (m, 2H), 0.44-0.34 (m, 2H). MS (ESI) 321 (M+H)$^+$.

Step E. 1-{[1-(Cyclopropylmethyl)-2-(2,2-dimethylpropyl)-1H-benzimidazol-5-yl]sulfonyl}-2-methylpropan-2-ol To a solution of 1-(cyclopropylmethyl)-2-(2,2-dimethylpropyl)-5-(methylsulfonyl)-1H-benzimidazole (Step D, 8.22 g, 25.7 mmol) in tetrahydrofuran (200 mL) was added lithium bis(trimethylsilyl)amide (1.07 M in hexane, 28.8 mL, 30.8 mmol) at −40° C. under nitrogen atmosphere. After stirring for 10 min, acetone (20 mL) was added at −40° C. and the mixture was allowed to warm to room temperature. After stirring for 18 h, the mixture was quenched with water (200 mL) and extracted with ethyl acetate (300 mL×3). The combined organic layers were dried over sodium sulfate and filtered. The filtrate was concentrated and the residue was purified by column chromatography on silica gel (hexane:ethyl acetate=3:2 as eluent) to afford the title compound (4.68 g, 48%) as a white solid.

$^1$H-NMR (CDCl$_3$) δ:8.33 (d, J=1.5 Hz, 1H), 7.80 (dd, J=8.8, 1.5 Hz, 1H), 7.50 (d J=8.8 Hz, 1H), 4.13 (d, J=6.6 Hz, 2H), 3.89 (s, 1H), 3.36 (s, 2H), 2.86 (s, 2H), 1.46 (s, 6H), 1.28-1.19 (m, 1H), 1.10 (s, 9H), 0.68-0.59 (m, 2H), 0.43-0.35 (m, 2H). MS (ESI) 379 (M+H)$^+$.

Step F. N-(2-{[1-(Cyclopropylmethyl)-2-(2,2-dimethylpropyl)-1H-benzimidazol-5-yl]sulfonyl}-1,1-dimethylethyl)formamide To a mixture of 1-{[1-(cyclopropylmethyl)-2-(2,2-dimethylpropyl)-1H-benzimidazol-5-yl]sulfonyl}-2-methylpropan-2-ol (Step E, 996 mg, 2.63 mmol) and trimethylsilyl cyanide (1.4 mL, 10.5 mmol) was added sulfuric acid (3 mL) at −30° C. The whole was warm to room temperature and stirred for 18 h. To the reaction mixture was added water at 0° C. and stirred for 1 h. Then, the resulting mixture was poured into potassium carbonate aqueous solution (20 mL) at 0° C. and extracted with dichloromethane (30 mL×3). The combined organic layer was dried over sodium sulfate and concentrated to afford the title compound (330 g, 31%) as a white amorphous.

$^1$H-NMR (CDCl$_3$) δ:8.33 (br, 1H), 7.97 (br s, 1H), 7.78 (dd, J=8.1, 1.5 Hz, 1H), 7.49 (d J=8.1 Hz, 1H), 6.01 (br s, 1H), 4.13 (d, J=6.6 Hz, 2H), 3.64 (s, 2H), 2.86 (s, 2H), 1.62 (s, 6H), 1.27-1.15 (m, 1H), 1.10 (s, 9H), 0.68-0.59 (m, 2H), 0.43-0.35 (m, 2H). MS (ESI) 406 (M+H)$^+$.

Step G. 1-{[1-(Cyclopropylmethyl)-2-(2,2-dimethylpropyl)-1H-benzimidazol-5-yl]sulfonyl}-2-methylpropan-2-amine A solution of N-(2-{[1-(cyclopropylmethyl)-2-(2,2-dimethylpropyl)-1H-benzimidazol-5-yl]sulfonyl}-1,1-dimethylethyl)formamide (Step F, 330 mg, 0.814 mmol) in Hydrogen Chloride, Methanol Reagent 10 (TCI Co.: 4 mL) was stirred at room temperature for 18 h. The reaction mixture was concentrated and the residue was extracted with dichloromethane (30 mL×3). The combined organic layer was washed with saturated sodium hydrogen carbonate aqueous solution (20 mL). The resulting solution was dried over sodium sulfate and concentrated. The residue was purified by column chromatography on silica gel (dichloromethane:methanol=15:1 as eluent) to afford the title compound (199 mg, 65%) as a white amorphous.

$^1$H-NMR (CDCl$_3$) δ:8.32 (br d, 1H), 7.81 (dd, J=8.1, 1.5 Hz, 1H), 7.49 (d J=8.8 Hz, 1H), 4.12 (d, J=6.6 Hz, 2H), 3.29 (s, 2H), 2.85 (s, 2H), 2.33 (br s, 2H), 1.38 (s, 6H), 1.23-1.14 (m, 1H), 1.10 (s, 9H), 0.67-0.59 (m, 2H), 0.43-0.35 (m, 2H). MS (ESI) 378 (M+H)$^+$.

Step H. N-(2-{[1-(Cyclopropylmethyl)-2-(2,2-dimethylpropyl)-1H-benzimidazol-5-yl]sulfonyl}-1,1-dimethylethyl) urea To a solution of 1-{[1-(cyclopropylmethyl)-2-(2,2-dimethylpropyl)-1H-benzimidazol-5-yl]sulfonyl}-2-methylpropan-2-amine (step G, 38 mg, 0.1 mmol) in dichloromethane (1.5 mL) were added triethylamine (28 μL, 0.2 mmol) and 4-nitrophenyl chloroformate (24 mg, 0.12 mmol) at 0° C. The mixture was stirred for 4 h at room temperature. To the resulting mixture was added ammonium hydroxide solution (25% in water; 20 μL, 0.12 mmol) and stirred continue to 20 h. The reaction was quenched by addition of saturated sodium 6 bicarbonate aqueous solution (10 mL) and water (10 mL). The organic phase was separated and the aqueous layer was extracted with dichloromethane (10 mL×2). The combined organic layer was washed with water (20 mL×4), brine (10 mL) and dried over sodium sulfate, filtered and concentrated. The residue was purified by silica gel TLC eluting with dichloromethane/methanol (10/1) to afford 16 mg (38%) of the title compound.

$^1$H-NMR (270 MHz, CDCl$_3$) $\delta$8.32 (d, J=1.4 Hz, 1H), 7.78 (dd, J=8.6, 1.4 Hz, 1H), 7.47 (d, J=8.6 Hz, 1H), 5.13 (bs, 1H), 4.27 (bs, 2H), 4.12 (d, J=6.5 Hz, 2H), 3.68 (s, 2H), 2.85 (s, 2H), 1.58 (s, 6H), 1.22-1.12 (m, 1H), 1.10 (s, 9H), 0.66-0.59 (m, 2H), 0.41-0.35 (m, 2H). MS (ESI) m/z 421 (M+H)$^+$.

Example 19

N-(2-{[1-(Cyclopropylmethyl)-2-(2,2-dimethylpropyl)-1H-benzimidazol-5-yl]sulfonyl}-1,1-dimethylethyl)acetamide

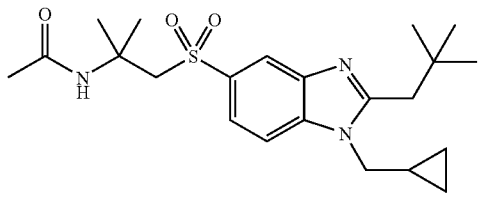

To a solution of 1-{[1-(cyclopropylmethyl)-2-(2,2-dimethylpropyl)-1H-benzimidazol-5-yl]sulfonyl}-2-methylpropan-2-amine (step G, of EXAMPLE 18, 39 mg, 0.1 mmol) in dichloromethane (0.5 mL) were added pyridine (0.016 mL, 0.2 mmol) and acetic anhydride (0.012 mL, 0.12 mmol) at room temperature. After 4 h, the reaction was quenched by addition of water (10 mL) and the organic layer was separated. The aqueous layer was extracted with dichloromethane (10 mL×2) and the combined organic layer was washed with water (10 mL), brine (5 mL) and dried over sodium sulfate, filtered and concentrated. The residue was purified by silica gel TLC eluting with hexane/ethyl acetate (1/5) to afford 33 mg (78%) of the title compound.

$^1$H-NMR (300 MHz, CDCl$_3$) $\delta$8.30 (d, J=1.5 Hz, 1H), 7.76 (dd, J=8.1, 1.5 Hz, 1H), 7.47 (d, J=8.1 Hz, 1H), 5.71 (bs, 1H), 4.12 (d, J=6.6 Hz, 2H), 3.69 (s, 2H), 2.85 (s, 2H), 1.79 (s, 3H), 1.57 (s, 6H), 1.23-1.14 (m, 1H), 1.10 (s, 9H), 0.66-0.59 (m, 2H), 0.41-0.35 (m, 2H). MS (ESI) m/z 420 (M+H)$^+$.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of the formula (I):

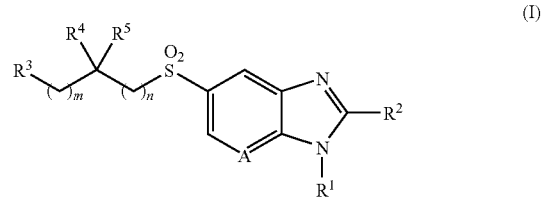

wherein

A is carbon or nitrogen;

R$^1$ is C$_1$-C$_4$ alkyl substituted with 1 to 2 substituents independently selected from the group consisting of C$_1$-C$_4$ alkyl, hydroxy, trifluoromethyl, trifluoromethoxy, C$_1$-C$_4$ alkoxy, amino, C$_1$-C$_4$ alkylamino, di(C$_1$-C$_4$ alkyl) amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl;

R$^2$ is cycloalkyl, alkyl-substituted cycloalkyl, C$_3$-C$_{10}$ alkyl, alkoxy-substituted C$_3$-C$_{10}$ alkyl or C$_1$-C$_2$ alkyl, said C$_1$-C$_2$ alkyl being substituted with 1 to 2 substituents independently selected from the group consisting of cycloalkyl and alkyl-substituted cycloalkyl;

R$^3$ is —NR$^a$CO—NR$^b$R$^c$, —NR$^a$CO—(C$_1$-C$_4$ alkyl), —CO—NR$^b$R$^c$, —NR$^a$SO$_2$—NR$^b$R$^c$ or —NR$^a$SO$_2$—(C$_1$-C$_4$ alkyl), wherein R$^a$, R$^b$ and R$^c$ are independently selected from hydrogen or C$_1$-C$_4$ alkyl, said C$_1$-C$_4$ alkyl optionally substituted with hydroxy, amino, C$_1$-C$_4$ alkylamino, di(C$_1$-C$_4$ alkyl)amino, aminocarbonyl, C$_1$-C$_4$ alkylaminocarbonyl, di(C$_1$-C$_4$ alkyl)aminocarbonyl or carboxy; or alternatively R$^b$ and R$^c$ together with nitrogen atom to which they are attached form a 5 to 6 membered ring;

R$^4$ and R$^5$ are independently selected from the group consisting of hydrogen, halogen, C$_1$-C$_4$ alkyl and C$_1$-C$_4$ alkoxy; or alternatively R$^4$ and R$^5$ together with the carbon atom to which they are attached form a 3 to 6 membered ring; and m and n are independently selected from 0, 1 or 2;

or a pharmaceutically acceptable salt thereof.

2. The compound or the pharmaceutically acceptable salt, as claimed in claim 1, wherein:

A is carbon or nitrogen; R$^1$ is C$_1$-C$_2$ alkyl substituted with 1 to 2 substituents independently selected from the group consisting of C$_1$-C$_4$ alkyl, hydroxy, trifluoromethyl, trifluoromethoxy, C$_1$-C$_4$ alkoxy, amino, C$_1$-C$_4$ alkylamino, di(C$_1$-C$_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl; R$^2$ is cycloalkyl, alkyl-substituted cycloalkyl, C$_3$-C$_{10}$ alkyl, alkoxy-substituted C$_3$-C$_{10}$ alkyl or C$_1$-C$_2$ alkyl, said C$_1$-C$_2$ alkyl being substituted with 1 to 2 substituents independently selected from the group consisting of cycloalkyl and alkyl-substituted cycloalkyl; R$^3$ is —NR$^a$CO—NR$^b$R$^c$, —NR$^a$CO—(C$_1$-C$_4$ alkyl), —CO—NR$^b$R$^c$ or —NR$^a$SO$_2$—(C$_1$-C$_4$ alkyl), wherein R$^a$, R$^b$ and R$^c$ are independently selected from hydrogen or C$_1$-C$_4$ alkyl, said C$_1$-C$_4$ alkyl optionally substituted with hydroxy, amino, C$_1$-C$_4$ alkylamino, di(C$_1$-C$_4$ alkyl) amino, aminocarbonyl, C$_1$-C$_4$ alkylaminocarbonyl, di(C$_1$-C$_4$ alkyl)aminocarbonyl or carboxy; or alternatively R$^b$ and R$^c$ together with nitrogen atom to which they are attached form a 5 to 6 membered ring; R$^4$ and R$^5$ are independently selected from the group consisting of hydrogen, halogen, C$_1$-C$_4$ alkyl and C$_1$-C$_4$ alkoxy; or alternatively R$^4$ and R$^5$ together with the carbon atom to which they are attached form a 3 to 6 membered ring; and m and n are independently selected from 0 or 1.

3. The compound or the pharmaceutically acceptable salt thereof, as claimed in claim 1, wherein:

A is carbon or nitrogen; R$^1$ is C$_1$-C$_2$ alkyl substituted with 1 to 2 substituents independently selected from the group consisting of C$_1$-C$_4$ alkyl, hydroxy, trifluoromethyl, trifluoromethoxy, C$_1$-C$_4$ alkoxy, amino, C$_1$-C$_4$ alkylamino, di(C$_1$-C$_4$ alkyl)amino, cycloalkyl, alkyl-substituted cycloalkyl, hydroxy-substituted cycloalkyl, amino-substituted cycloalkyl, heterocyclyl, alkyl-substituted heterocyclyl and hydroxy-substituted heterocyclyl; R$^2$ is alkyl-substituted C$_3$-C$_6$ cycloalkyl, C$_4$-C$_8$ alkyl, alkoxy-substituted C$_4$-C$_8$ alkyl, or methyl substituted with one substituent selected from the group consisting of C$_3$-C$_5$ cycloalkyl and alkyl-substituted C$_3$-C$_5$ cycloalkyl; R$^3$ is —NR$^a$CO—NR$^b$R$^c$, —NR$^a$CO—(C$_1$-C$_4$ alkyl), —CO—NR$^b$R$^c$ or —NR$^a$SO$_2$—(C$_1$-C$_4$ alkyl), wherein R$^a$, R$^b$ and R$^c$ are independently selected from hydrogen or C$_1$-C$_4$ alkyl, said C$_1$-C$_4$ alkyl optionally substituted with hydroxy, amino, C$_1$-C$_4$ alkylamino, di(C$_1$-C$_4$ alkyl)amino, aminocarbonyl, C$_1$-C$_4$ alkylaminocarbonyl, di(C$_1$-C$_4$ alkyl)aminocarbonyl or carboxy; R$^4$ and R$^5$ are independently selected from hydrogen or C$_1$-C$_4$ alkyl; or alternatively R$^4$ and R$^5$ together with the carbon atom to which they are attached form a 3 to 6 membered ring; and m and n are independently selected from 0 or 1.

4. The compound of claim 1, which is selected from:
2-{[1-(cyclopropylmethyl)-2-(2,2-dimethylpropyl)-1H-benzimidazol-5-yl]sulfonyl}-2-methylpropanamide;
1-{[1-(cyclopropylmethyl)-2-(2,2-dimethylpropyl)-1H-benzimidazol-5-yl]sulfonyl}cyclopropanecarboxamide;
1-{[1-(cyclopropylmethyl)-2-(2,2-dimethylpropyl)-1H-benzimidazol-5-yl]sulfonyl}cyclobutanecarboxamide;
4-{[1-(cyclopropylmethyl)-2-(2,2-dimethylpropyl)-1H-benzimidazol-5-yl]sulfonyl}tetrahydro-2H-pyran-4-carboxamide; and
2-{[3-(cyclopropylmethyl)-2-(2,2-dimethylpropyl)-3H-imidazo[4,5-b]pyridin-6-yl]sulfonyl}-2-methylpropanamide;
or a pharmaceutically acceptable salt thereof.

5. The compound of claim 1, which is selected from:
2-{[1-(cyclopropylmethyl)-2-(2,2-dimethylpropyl)-1H-benzimidazol-5-yl]sulfonyl}-N,N,2-trimethylpropanamide;
2-{[1-(cyclopropylmethyl)-2-(2,2-dimethylpropyl)-1H-benzimidazol-5-yl]sulfonyl}-N-(2-hydroxyethyl)-2-methylpropanamide;
N-(2-{[1-(cyclopropylmethyl)-2-(2,2-dimethylpropyl)-1H-benzimidazol-5-yl]sulfonyl}-2-methylpropyl)methanesulfonamide;
N-(2-{[1-(cyclopropylmethyl)-2-(2,2-dimethylpropyl)-1H-benzimidazol-5-yl]sulfonyl}-2-methylpropyl)-N'-methylurea; and
N-(2-{[1-(cyclopropylmethyl)-2-(2,2-dimethylpropyl)-1H-benzimidazol-5-yl]sulfonyl}-2-methylpropyl)urea;
or a pharmaceutically acceptable salt thereof.

6. A pharmaceutical composition comprising the compound or the pharmaceutically acceptable salt thereof, of claim 1 and a pharmaceutically acceptable carrier.

7. The pharmaceutical composition as claimed in claim 6 further comprising another pharmacologically active agent.

* * * * *